United States Patent [19]

Symonds et al.

[11] Patent Number: 6,114,167
[45] Date of Patent: *Sep. 5, 2000

[54] RIBOZYMES TARGETING THE MOMLV PSI PACKAGING SEQUENCE AND THE HIV TAT SEQUENCE

[75] Inventors: Geoffrey P. Symonds, Rose Bay; Lun-Quan Sun, Ryde, both of Australia

[73] Assignee: Gene Shears Pty., Ltd., New South Wales, Australia

[*] Notice: This patent is subject to a terminal disclaimer.

[21] Appl. No.: 08/310,259

[22] Filed: Sep. 21, 1994

Related U.S. Application Data

[63] Continuation-in-part of application No. 08/178,082, Jan. 5, 1994, Pat. No. 5,712,384.

[51] Int. Cl.$^7$ ................................................ C12N 5/10
[52] U.S. Cl. ................. 435/372.3; 435/325; 435/366
[58] Field of Search .................... 435/91.31, 172.3, 435/240.2, 252.3, 320.1, 325, 366, 372.3; 514/44; 536/23.1, 23.2, 24.5

[56] References Cited

U.S. PATENT DOCUMENTS

| | | | |
|---|---|---|---|
| 5,525,468 | 6/1996 | McSwiggen | 435/6 |
| 5,693,535 | 12/1997 | Draper et al. | 435/372.3 |

FOREIGN PATENT DOCUMENTS

WO9217211  10/1992  WIPO.

OTHER PUBLICATIONS

Cech et al. (1992) Ribozyme engineering. Curr. Opin. Structural Biol. 2:605–609.
Goodchild (1992) Enhancement of ribozyme catalytic activity by a contiguous oligodeoxynucleotide (facilitator) and by 2'-O-methylation. Nucleic Acids Res. 20:4607–4612.
Dropulic et al. (1992) J. Virol. 66:1432–1441.
Sarver et al. (1992) Aids Res. Rev. 2:259–285.
Berzal–Herranz, A. et al. (1993) "Essential Nucleotide Sequences and Secondary Structure Elements of the Hairpin Ribozyme," EMBO 12:2567–2674.
Bevec, D. et al. (1992) "Inhibition of Human Inmmunodeficiency Virus Type 1 Replication in Human T Cells by Retroviral–Mediated Gene Transfer of a Dominant–Negative Rev Trans–Activator," Proc. Natl. Acad. Sci. (USA) 89:9870–9874.
Bischofberger, N. and Wagner, R.W. (1992) "Antisense Approaches to Antiviral Agents," Virology 3:57–66.
Chen, C–J. et al. (1992) "Inhibition of HIV–1 Replication by Novel Multitarget Ribozymes," Ann. N.Y. Acad. Sci. (USA) 660:271–273.
Chen, C–J. et al. (1992) "Multitarget–Ribozyme Directed to Cleave at up to Nine Highly Conserved HIV–1 env RNA Regions Inhibits HIV–1 Replication—Potential Effectiveness Against Most Presently Sequenced HIV–1 Isolates, "Nucleic Acids Res. (Eng.) 20:4581–4589.
Chowrira, B.M. et al. (1993) "Four Ribose 2'-Hydroxyl Groups Essential for Catalytic Function of the Hairpin Ribozyme,"J. Biol. Chem. 268:19458–119462.
Cournoyer, D. and Caskey, C.T. (1993) "Gene Therapy of the Immune System," Annu. Rev. Immunol. (USA) 11:297–329.
Crisell, P. et al. (1993) "Inhibition of HIV–1 Replication by Ribozymes that Show Poor Activity in vitro," Nucleic Acids Res. (Eng.) 21:5251–5255.
Dropulic, B. et al. (1993) "Ribozymes: Use As Anti–HIV Therapeutic Molecules," Antisense Res. Dev. (USA) 3:87–94.
Goodchild, J. (1991) "Antisense Antivirals," Antisense Res. Dev. (USA) 1:361–364.
Heidenreich, O. and Eckstein, F. (1992) "Hammerhead Ribozyme–Mediated Cleavage of the Long Terminal Repeat RNA of Human Immunodeficiency Virus Type 1," J. Biol. Chem. (USA) 267:1904–1909.
Homann, M. et al. (1993) "Incorporation of the Catalytic Domain of a Hammerhead Ribozyme Into Antisense RNA Enhances Its Inhibitory Effect on the Replication of Human Immunodeficiency Virus Type 1," Nucleic Acids Res. (Eng.) 21:2809–2814.
Johnston, M.I. and Burke, J.M. (1993) "Present Status and Future Prospects for HIV Therapies," Science 260:1286–1293.
Joseph, S. et al. (1993) "Optimization of an Anti–HIV Hairpin Ribozyme Determined by in Vitro Selection," J. Biol. Chem. (USA) 268:24515–24518.
Joseph, S. et al. (1993) "Substrate Selection Rules for the Hairpin Ribozyme Determined by in Vitro Selection, Mutation, and Analysis of Mismatched Substrates," Genes and Development 7:130–138.
Levy, J. (1993) "Pathogenesis of Human Immunodeficiency Virus Infection," Microbiol. Rev. 57:183–289.
Lisziewicz, J. et al. (1993) "Inhibition of Human Immunodeficiency Virus Type 1 Replication By Regulated Expression of a Polymeric Tat Activation Response RNA Decoy as a Strategy For Gene Therapy in AIDS," Proc. Natl. Acad. Sci. USA 90:8000–8004.
Liu, J. et al. (1994) "Regulated Expression of a Dominant Negative Form of Rev Improves Resistance to HIV Replication in T Cells," Gene Therapy (Eng.) 1:32–37.
Lo, K.M. et al.(1992) "Inhibition of Replication of HIV–1 by Retroviral Vectors Expessing tat–Antisense and Anti–tat Ribozyme RNA" Virology (USA) 190:176–183.

(List continued on next page.)

*Primary Examiner*—Robert A. Schwartzman
*Attorney, Agent, or Firm*—John P. White; Cooper & Dunham LLP

[57] ABSTRACT

A cell comprising a synthetic non-naturally occurring oligonucleotide compound comprises nucleotides whose sequence defines a conserved catalytic region and nucleotides whose sequence hybridizes with a predetermined target sequence within a MoMLV Psi packaging sequence on the HIV tat sequence. The catalytic region may be derived from a hammerhead ribozyme, a hairpin ribozyme a hepatitis delta ribozyme, an PNAase P ribozyme, a group I intron or a group II intron.

12 Claims, 22 Drawing Sheets

OTHER PUBLICATIONS

Lori, F. et al.(1994) "Rapid Protection Against Human Immunodeficiency Virus Type 1 (HIV–1) Replication Mediated by High Efficiency Non–retroviral Delivery of Genes Interfering with HIV–1 tat and gag," Gene Therapy (Eng.) 1:27–31.

Ohkawa, J. et al. (1993) "Importance of Independence in Ribozyme Reactions: Kinetic Behavior of Trimmed and of Simply Connected Multiple Ribozymes with Potential Activity Against Human Immunodeficiency Virus," Proc. Natl. Acad. Sci. USA 90:11302–11306.

Ohkawa, J. et al. (1993) "Multiple Site–Specific Cleavage of HIV RNA by Transcribed Ribozymes from Shotgun–Type Trimming Plasmid," Nucleic Acids Symp. Ser (Eng.) 29:121–122.

Ojwang, J.O. et al. (1992) "Inhibition of Human Immunodeficiency Virus Type 1 Expression by a Hairpin Ribozyme," Proc. Natl. Acad. Sci. USA 89:10802–10806.

Rossi, J.J. et al. (1992) "Catalytic Antisense RNA (Ribozymes): Their Potential and Use as Anti–HIV–1 Therapeutic Agents," Adv. Exp. Med. Biol. (USA) 312:95–109.

Rossi, J.J. et al. (1992) "Ribozymes as Anti–HIV–1 Therapeutic Agents: Principles, Applications, and Problems," AIDS Res. Hum. Retroviruses (USA) 8:183–189.

Rossi, J.J. et al. (1990) "Ribozymes as Therapies for AIDS," Ann. N.Y. Acad. Sci. (USA) 616:184–200.

Sarver, N. (1991) "Ribozymes: A New Frontier in Anti–HIV Strategy," Antisense Res. Dev. (USA) 1:373–378.

Sarver, N. et al. (1990) "Ribozymes as Potential Anti–HIV–1 Therapeutic Agents," Science 247:1222–1225.

Shimayama, T. et al. (1993) "Cleavage of the Highly Conserved Hairpin–Loop Region of HIV–1 by Synthetic Ribozymes," Nucleic Acids Symp. Ser. (Eng.) 29:177:178.

Taylor, N.R. and Rossi, J.J. (1991) "Ribozyme–Mediated Cleavage of an HIV–1 gag RNA: The Effects of Nontargeted Sequences and Secondary Structure on Ribozyme Cleavage Activity," Antisense Res. Dev. 1:173–186.

Thill, G. et al. (1993) "Structural and Sequence Elements Required for the Self–Cleaving Activity of the Hepatitis Delta Virus Ribozyme," Biochemistry 32:4254–4262.

Weerasinghe, M. et al. (1991) Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme J. Virol (USA) 65:5531–5534.

Yamada, O. et al. (1994) "Intracellular Immunization of Human T Cells with a Hairpin Ribozyme Against Human Immunodeficiency Virus Type 1," Gene Therapy (Eng.) 1:38–45.

Yu, M. et al. (1993) "A Hairpin Ribozyme Inhibits Expression of Diverse Strains of Human Immunodeficiency Virus Type 1," Proc. Natl. Acad. Sci. USA 90:6340–6344.

Zaia, J.A. et al. (1992) "Status of Ribozyme and Antisense–Based Developmental Approaches for Anti–HIV–1 Therapy," Ann. N.Y. Acad. Sci. (USA) 660:95–106.

RETROVIRAL REPLICATION CYCLE

ANTI-MoMLV RIBOZYME TARGETING SITES

MOLONEY MURINE LEUKEMIA VIRUS

STANDARD RIBOZYME CONSTRUCT

ANTI-HIV RIBOZYME (ψ SITE)

Anti – HIV-1 tat Ribozymes

FIGURE 12

Sequence Conservation of RzM Target Regions
Among HIV-1 Isolates

| Target | A | TTG | GGT | GTC | AAC | ATA | GC**** | GAG | CCA | GTA | GAT | CCT | A**** | CAG | GAA | GTC | AGC | CTA | GG |
|---|---|---|---|---|---|---|---|---|---|---|---|---|---|---|---|---|---|---|---|
| SP2 | - | --- | --- | --- | --- | --- | -- | --- | --- | --- | --- | --- | - | --- | --- | --- | --- | --- | AA |
| BRU | - | --- | --- | --- | G-- | --- | -- | --- | --- | --- | --- | --- | - | --- | --- | --- | --- | --- | AA |
| HXB2 | - | --- | --- | --- | G-- | --- | -- | --- | --- | --- | --- | --- | - | --- | --- | --- | --- | --- | AA |
| HAN | - | --- | --- | --- | GC- | --- | -- | --- | --- | --- | --- | --- | - | --- | --- | --- | --- | --- | AA |
| NDK | - | --- | --- | --- | --- | G-- | -- | --- | --- | --- | --- | --- | - | --- | --- | --- | --- | --- | -- |
| MAL | - | --- | --- | --- | --- | G-- | -- | --- | --- | --- | --- | --- | - | --- | -G- | --- | --- | --- | -- |
| MN | - | --- | --- | --- | G-- | --- | -- | --- | --- | --- | --- | --- | - | --- | --- | --- | --- | --- | A- |
| SC | - | --- | --- | --- | G-- | --- | -- | --T | --- | --- | --- | --- | - | --- | --- | --- | --- | --- | AA |
| OYI | - | --- | --- | --- | --- | --- | -- | --- | --- | --- | --- | --- | - | --- | --- | --- | --- | --- | A- |
| RF | - | --- | --- | --- | --- | G-- | -- | --- | --- | --- | --- | --- | - | --- | --- | --- | --- | --- | A- |
| ELI | - | --- | --- | --- | --- | G-- | -- | --- | --- | --- | --- | --- | - | --- | --- | --- | --- | --- | -- |
| Z2 | - | --- | --- | --- | --- | G-- | -- | --- | --- | --- | --- | --- | - | --- | --- | --- | --- | --- | A- |
| Z6 | - | --- | --- | --- | --- | --- | -- | --T | --- | --- | --- | --- | - | --- | --- | --- | --- | -A- | -A |
| PV22 | - | --- | --- | --- | G-- | --- | -- | --- | --- | --- | --- | --- | - | --- | --- | --- | --- | --- | AA |
| BH10 | - | --- | --- | --- | G-- | --- | -- | --- | --- | --- | --- | --- | - | --- | --- | --- | --- | --- | -- |
| BH5 | - | --- | --- | --- | G-- | --- | -- | --- | --- | --- | --- | --- | - | --- | --- | --- | --- | --- | -A |
| HXB3 | - | --- | --- | --- | G-- | --- | -- | --- | --- | --- | --- | --- | - | --- | --- | --- | --- | --- | -- |
| CDC451 | - | --- | --- | --- | GG- | --- | -- | --- | --- | --- | --- | --- | - | --- | --- | --- | --- | --- | -A |

FIGURE 13

COMPARISON OF RIBOZYME TARGET SITES OF ANTI-tat RIBOZYMES

```
5781           5792                              5849                    5886        5900
CAGAATTGGG TGTCAACATA GCAGAATAGG......TGGAGCCAGT AGATCCTAAT......AGGAAGTCAG CCTAGGACTG
                  Site 1                              Site 2                 Site 3
```

Note: The sequence is from HIV-1 SF2 strain

Experiment 4: Total PBLs (Ribozyme Constructs)

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:1:

NCUGANGANN NNNNGAAAN                                    19

(2) INFORMATION FOR SEQ ID NO:2:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:2:

NCUGANGANG AAAN                                        14

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

NGANNGAAAC NNNANANUAC N                                21

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:4:

TTAGGATCCT GATGAGTCCG TGAGGACGAA ACTGGCTC                38

(2) INFORMATION FOR SEQ ID NO:5:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (xi) SEQUENCE DESCRIPTION: SEQ ID NO:5:

```
CCTAGGCTCT GATGAGTCCG TGAGGACGAA ACTTCCTGTT AGGATCCTGA TGAGTCCGTG      60

AGGACGAAAC TGGCTCGCTA TGTTCTGATG AGTCCGTGAG GACGAAACAC CCAA           114
```

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:6:

```
GTCAAAAATT GGCGCTGATG AGTCCGTGAG GACGAAACTC ACCAGTCGCC G               51
```

(2) INFORMATION FOR SEQ ID NO:7:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (xi) SEQUENCE DESCRIPTION: SEQ ID NO:7:

```
GUGGCGCCCG AACAGGGACG CGAAAGCGAA AGUAGAACCA GAGGAGCUCU CUCGACGCAG      60

GACUCGGCUU GCUGAAGCGC GCACAGCAAG AGGCGAGGGG CGGCGACUGG UGAGUACGCC     120

AAUUUUUGAC UAGCGGAGGC UAGAAGGAGA GAGAGAUGGG UGCGAGAGCG               170
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GGAGCCAGTA GATCCTA                                                    17
```

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATTGGGTGTC AACATAGC                                                   18
```

```
(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GAGCCAGTAG ATCCT                                                          15

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CAGGAAGTCA GCCTAGG                                                        17

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAGAATTGGG TGTCAACATA GCAGAATAGG                                          30

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TGGAGCCAGT AGATCCTAAT                                                     20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AGGAAGTCAG CCTAGGACTG                                                     20
```

RIBOZYMES TARGETING THE MOMLV PSI PACKAGING SEQUENCE AND THE HIV TAT SEQUENCE

This application is a continuation-in-part of U.S. Ser. No. 08/178,082, filed Jan. 5, 1994, U.S. Pat. No. 5,712,384. Throughout this application various publications are referred to by author and year within brackets. The full references are listed alphabetically after the Experimental Section. The disclosures for these publications in their entireties are hereby incorporated by reference into this application to more fully describe the state of the art to which this invention pertains.

BACKGROUND OF THE INVENTION

RETROVIRUSES

Retroviruses are viruses with RNA as their genomic material. They use host cells for their replication by stably integrating a cDNA copy of their genomic RNA into the host cell genome (Miller, 1992, and Brown, 1987). The viral genome consists of a Long Terminal Repeat (LTR) at each end (5' and 3') of the proviral cDNA form of the virus. Proceeding from 5' to 3', the LTR consists of U3 and U5 sequences linked by a short sequence termed R. Transcription commences within the 5' LTR and terminates at a polyadenylation site within the 3' LTR. Adjacent to the LTRs are short sequences necessary for priming of positive and negative strand DNA synthesis by reverse transcriptase. Splice donor and acceptor sequences are also present within the genome and these are involved in the production of sub-genomic RNA species. Directly proximal to the 5' LTR is a sequence necessary for the encapsidation of viral RNA into virions. This is termed the Psi packaging sequence. It is an essential and specific signal ensuring that the viral RNA is packaged. The bulk of the viral RNA consists of the gag, pol and env replicative genes which encode, respectively, core proteins (gag), the enzymes integrase, protease and reverse transcriptase (pol), and envelope proteins (env).

Retroviral infection of a cell is initiated by the interaction of viral glycoproteins with cellular receptors (A) (see FIG. 1). Following adsorption and uncoating, the viral RNA enters the target cell and is converted into cDNA by the action of reverse transcriptase, an enzyme brought within the virion (B). The cDNA adopts a circular form (C), is converted to double-stranded cDNA and then becomes integrated into the host cell's genomic DNA by the action of integrase (D). Once integrated, proviral cDNA is transcribed from the promoter within the 5' LTR (E). The transcribed RNA either acts as mRNA and is translated to produce the viral proteins (F) or is left as nascent viral RNA. This viral RNA contains a Psi packaging sequence which is essential for its packaging into virions (G). Once the virion is produced, it is released from the cell by budding from the plasma membrane (H). In general, retroviruses do not cause lysis of the host cell; HIV is an exception to this. The proviral cDNA remains stably integrated in the host genome and is replicated with the host DNA so that progeny cells also inherit the provirus. Potential anti-viral agents may be targeted at any of these replicative control points.

HUMAN IMMUNODEFICIENCY VIRUS (HIV)

HIV belongs to the class retrovirus and its replication is as outlined above. The entry of HIV into cells, including T lymphocytes, monocytes and macrophages, is generally effected by the interaction of the gp120 envelope protein of HIV with a CD4 receptor on the target cell surface. The amino acid sequence of gp120 can be highly variable in different patients (or even the same patient) making vaccine production very difficult (Brown, 1987 and Peterlin et al., 1988). This variability appears to be associated with disease progression. The major peculiarities for HIV are i) that (as for other members of the group lentivirus) it has a latent phase in which the provirus may lie dormant following integration into the host cell's genome, and ii) it is cytopathic for T lymphocyte target cells. HIV commences replication after cells which harbor the provirus are activated. The stimulus (or stimuli) for cell activation and accompanying viral replication have not yet been clearly identified (Brown, 1987 and Peterlin et al., 1988). As for all retroviruses, gag, pol and env gene products are translated into structural and enzymatic proteins. In the case of HIV, there are additional regulatory genes. Specifically, tat and rev gene products are translated into regulatory proteins and act as transcriptional enhancers to induce high levels of gene expression. Nef is another regulatory gene which serves to modulate viral replication levels (Jones, 1989, Greene, 1990, and Epstein, 1991).

HIV replication is highest in activated and proliferating cells; cellular activation leads to the binding of nuclear transcription and cellular enhancer factors to the HIV LTR which results in increased levels of transcription. As for all retroviruses, the packaging region (Psi) is a cis-acting RNA sequence present on the HIV genome, necessary for encapsidation of the genomic RNA. The formation of a core incorporating gag proteins, pol enzymes and viral RNA is the last stage of the HIV replication cycle. This core obtains a membrane and leaves the cell by budding through the cell membrane (Peterlin et al., 1988, Jones, K. A., 1989, Greene, 1990, and Epstein, 1991).

To date, a number of agents for the suppression of HIV replication have been studied. a description follows of certain agents that have been targeted at the replicative stages represented in FIG. 1.

(A) Viral Adsorption to the Target Cell

Soluble CD4 has been used in an attempt to occupy a high proportion of the viral receptors so that the virus is unable to bind to the cell membrane. However, to date this has not been found to be a successful therapeutic strategy (Stevenson et al., 1992). Sulphated polysaccharides have demonstrated an ability to inhibit HIV infection possibly by interrupting cell-virus fusion (McClure et al., 1992). Antibodies to HIV itself, the host cell receptors or HIV envelope determinants as well as CD4 conjugated exotoxin (Stevenson et al., 1992) are other possible methods of interrupting viral entry into a cell.

(B) Production of cDNA by Reverse Transcriptase

Chemicals such as azidothymidine triphosphate (AZT) have been found to inhibit reverse transcriptase in vitro. AZT is presently administered both routinely to AIDS patients and when they receive bone marrow transplants, the latter in an attempt to protect the normal marrow from residual HIV (Miller, 1992).

(C) Translocation of the cDNA from the Cytoplasm to the Nucleus

It may be possible to interrupt cDNA translocation across nuclear pores or nuclear transport itself but this has not yet been shown to be successful.

(D) Integration of the cDNA into the Host Genome

It may also be possible to block the integration of the proviral cDNA into the host cell genome (Stevenson et al., 1992). To date, there are no candidate compounds which have proven effective.

(E) Proviral Transcription 5,6-dichloro-1-beta-D-ribofuranosyl benzimidazole is known to interfere with transcriptional elongation (Stevenson et al., 1992). Sense TAR analogs may also affect transcription by binding the tat protein thereby inhibiting its ability to activate HIV (Miller, 1992 and Sullenger et al., 1990).

(F) Translation of HIV mRNA

Antisense RNA, by binding to viral RNA, may inhibit viral replication (Sczakiel et al., 1992). Binding to mRNA may serve to inhibit translation; binding to the nascent viral RNA may also act to inhibit productive packaging of RNA into virions.

(G) Viral Packaging and Production of Mature Virions

Protease induces specific cleavage of the HIV polyprotein. This activity is essential for production of mature, infectious virions. Several compounds such as α,α-difluoroketones, have been found to inhibit HIV protease and have shown a degree of anti-viral activity in tissue culture. However, most protease inhibitors have displayed short serum half-life, rapid biliary clearance and poor oral availability (Debouck, 1992).

RIBOZYMES

Ribozymes are enzymatic RNAs that cleave RNA and exhibit turnover. In some classes of ribozymes by the addition of complementary sequence arms, they can be rendered capable of pairing with a specific target RNA and inducing cleavage at specific sites along the phosphodiester backbone of RNA (Haseloff et al., 1988; Rossi et al., 1992; Hampel, 1990; Ojwang, 1992). The hammerhead ribozyme is small, simple and has an ability to maintain site-specific cleavage when incorporated into a variety of flanking sequence motifs (Haseloff et al., 1988; Rossi et al., 1992). These features make it particularly well suited for gene suppression.

SUMMARY OF THE INVENTION

This invention is directed to a synthetic non-naturally occurring oligonucleotide compound which comprises nucleotides whose sequence defines a conserved catalytic region and nucleotides whose sequence is capable of hybridizing with a predetermined target sequence within a packaging sequence of an RNA virus. Preferably, the viral packaging sequence is a retrovirus packaging sequence and in one embodiment the HIV-1 Psi packaging sequence. The RNA virus may be HIV-1, Feline Leukemia Virus, Feline Immunodeficiency Virus or one of the viruses listed in Table I. The conserved catalytic region may be derived from a hammerhead ribozyme, a hairpin ribozyme, a hepatitis delta ribozyme, an RNAase P ribozyme, a group I intron, a group II intron. The invention is also directed to multiple ribozymes, and combinations of ribozymes and antisense targeted against the RNA virus and such combinations further including polyTAR, RRE or TAR decoys. Vectors or ribozymes with or without antisense and polyTAR, RRE or TAR decoys are also described. Further, methods of treatment and methods of use both in vivo and ex vivo are described.

BRIEF DESCRIPTION OF THE FIGURES

FIG. 12. Tat conserved sequence (SEQ ID NOs. 9–11)

FIG. 13. Comparison of various tat target sequences (SEQ ID NOs. 12–14)

DETAILED DESCRIPTION OF THE INVENTION

Figure 1:
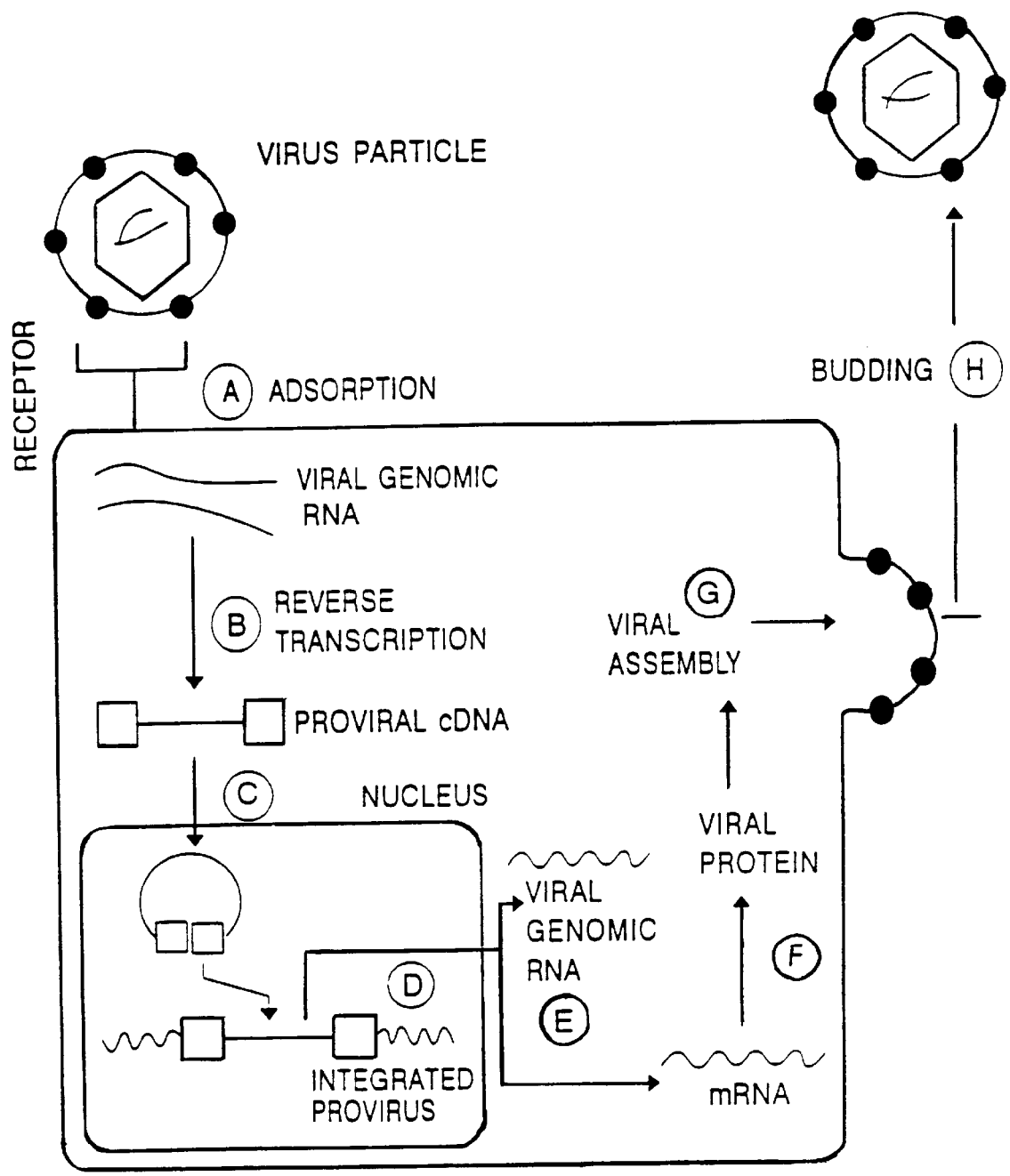
FIG. 1. Replication cycle of a typical retrovirus.
(A) Virus binds to cell surface receptors on the target cell and the genomic RNA enters the target cell following fusion and viral uncoating.
(B) Reverse transcription occurs resulting in the conversion of viral RNA into cDNA.
(C) cDNA enters the nucleus and is converted into a circular form.
(D) The cDNA then becomes integrated into the host cell genome.
(E) Transcription of the provirus to produce viral RNA and mRNA.
(F) Translation produces viral proteins.
(G) The viral core is formed from the virally encoded proteins and viral RNA packaged.
(H) The core obtains a membrane and exits the cell by budding through the cell membrane.

This invention is directed to a synthetic non-naturally occurring oligonucleotide compound which comprises nucleotides whose sequence defines a conserved catalytic region and nucleotides whose sequence is capable of hybridizing with a predetermined target sequence within a packaging sequence of an RNA virus. Preferably, the viral packaging sequence of is a retrovirus packaging sequence and in one embodiment the HIV-1 Psi packaging sequence. The RNA virus may be HIV-1, Feline Leukemia Virus, Feline Immunodeficiency Virus or one of the viruses listed in Tables 6–7. The conserved catalytic region may be derived from a hammerhead ribozyme (see Haseloff et al. U.S. Pat. No. 5,245,678; Rossi et al. U.S. Pat. No. 5,249,796), a hairpin ribozyme (see Hampel et al., European Application No. 89 117 424, filed Sep. 20, 1989), a hepatitis delta ribozyme (Goldberg et al. PCT International Application Nos. WO 91/04319 and WO 91/04324, published Apr. 4, 1991), an RNAase P ribozyme (see Altman et al., U.S. Pat. No. 5,168,053), a group I intron (see Cech et al. U.S. Pat. No. 4,987,071), or a group II intron (see Pyle, 1993).

In one embodiment the compound may have the structure: (SEQ ID NO.1)

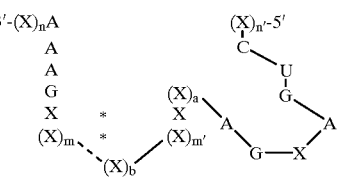

wherein each X represents a nucleotide which is the same or different and may be modified or substituted in its sugar, phosphate or base; wherein each of A, C, U, and G represents a ribonucleotide which may be unmodified or modified or substituted in its sugar, phosphate or base; wherein 3'—AAG . . . AGUCX—5' defines the conserved catalytic region; wherein each of $(X)_n A$ and $(X)_{n'}$ defines the nucleotides whose sequence is capable of hybridizing with the predetermined target sequence within the packaging sequence of the RNA virus; wherein each * represents base pairing between the nucleotides located on either side thereof; wherein each solid line represents a chemical linkage providing covalent bonds between the nucleotides located on either side thereof; wherein a represents an integer which defines a number of nucleotides with the proviso that a may be 0 or 1 and if 0, the A located 5' of $(X)_a$ is bonded to the X located 3' of $(X)_a$; wherein each of m and m' represents an integer which is greater than or equal to 1; wherein $(X)_b$ represents an oligonucleotide and b represents an integer which is greater than or equal to 2.

Alternatively, the compound may have the structure: SEQ ID NO:2

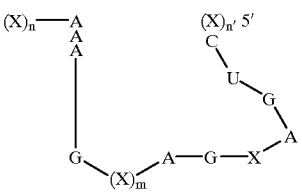

wherein 3'—AAG . . . AGUCX—5' defines the conserved catalytic region; wherein m represents an integer from 2 to 20; and wherein none of the nucleotides $(X)_m$ are Watson-Crick base paired to any other nucleotide within the compound.

In another embodiment, the compound of claim 1 having the structure: (SEQ ID NO:3)

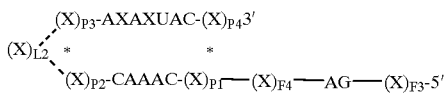

wherein 3'$(X)_{P4}$ ... $(X)_{P1}$—5' defines the conserved catalytic region; wherein each of $(X)_{F4}$ and $(X)_{F3}$ defines the nucleotides whose sequence is capable of hybridizing with the predetermined target sequence within the packaging sequence of an RNA virus; wherein each solid line represents a chemical linkage providing covalent bonds between the nucleotides located on either side thereof; wherein F3 represents an integer which defines the number of nucleotides in the oligonucleotide with the proviso that F3 is greater than or equal to 3; wherein F4 represents an integer which defines the number of nucleotides in the oligonucleotide with the proviso that F4 is from 3 to 5; wherein each of $(X)_{P1}$ and $(X)_{P4}$ represents an oligonucleotide having a predetermined sequence such that $(X)_{P4}$ base-pairs with 3–6 bases of $(X)_{P1}$; wherein P1 represents an integer which defines the number of nucleotides in the oligonucleotide with the proviso that P1 is from 3 to 6 and the sum of P1 and F4 equals 9; wherein each of $(X)_{P2}$ and $(X)_{P3}$ represents an oligonucleotide having a predetermined sequence such that $(X)_{P2}$ base-pairs with at least 3 bases of $(X)_{P3}$; wherein each of the dashed lines independently represents either a chemical linkage providing covalent bonds between the nucleotides located on either side thereof or the absence of any such chemical linkage; and wherein $(X)_{L2}$ represents an oligonucleotide which may be present or absent with the proviso that L2 represents an integer which is greater than or equal to 3 if $(X)_{L2}$ is present.

In another embodiment, the nucleotides whose sequences define a conserved catalytic region are from the hepatitis delta virus conserved region. Alternately, the nucleotides whose sequences define a conserved catalytic region contain the sequence NCCA at its 3' terminus.

The invention is also directed to multiple compounds or ribozymes with conserved catalytic regions which may be the same or different targeted to predetermined target sequences which may be the same or different. In this embodiment, a synthetic non-naturally occurring oligonucleotide compound which comprises two or more domains which may be the same or different wherein each domain comprises nucleotides whose sequence defines a conserved catalytic region and nucleotides whose sequence is capable of hybridizing with a predetermined target sequence within a packaging sequence of an RNA virus. The compounds may also be covalently linked to an antisense nucleic acid compound capable of hybridizing with a predetermined sequence, which may be the same as or different from the oligonucleotide compound, within a packaging sequence of the RNA virus.

In one preferred embodiment, the nucleotides are capable of hybridizing with the 243, 274, 366 or 553 target sequence in the MoMLV and site 749 in the HIV Psi packaging site. The oligonucleotide compounds may further comprise at least one additional synthetic non-naturally occurring oligonucleotide compound or antisense molecule covalently linked, targeted to a different gene of the RNA virus genome. In the case where the RNA virus is HIV and the different region of the HIV genome may be selected from the group consisting of long terminal repeat, 5' untranslated region, splice donor-acceptor sites, primer binding sites, 3' untranslated region, gag, pol, protease, integrase, env, tat, rev, nef, vif, vpr, vpu, vpx, or tev region.

Preferably, the first oligonucleotide compound is capable of hybridizing with the 243, 274, 366 or 553 target sites or combination thereof in the MoLV and site 749 in the HIV Psi packaging site and the nucleotides of the second additional compound are capable of hybridizing with the 5792, 5849, 5886, or 6042 target sites or combination thereof in the HIV tat region. Additional targets may be found within the HIV genome, particularly within the tat sequence and within the psi packaging region (HIV-1 SF2) (SEQ ID NO:7) 636 GUGGC GCCCG AACAG GGACG CGAAA GCGAA A GUAG AACCA GAGGA GCUCU CUCGA CGCAG GA CUC GGCUU GCUGA AGCGC GCACA GCAAG AGGCG AGGGG CGGCG ACUGG UGAGU ACGCC AA UUU UUGAC UAGCG GAGGC UAGAA GGAGA GAGAG AUGGG UGCGA GAGCG 805. The specific ribozyme sequences used here are Rz-2, Rz-M and Rz-ψ. The Anti-HIV Ribozyme Sequences Rz-2 (single anti-tat) (SEQ ID NO:4) TTAGGATCCTGATGAGTCCGTGAG-GACGAAACTGGCTC Rz-M (multiple anti-tat) (SEQ ID NO:5) CCTAGGCTCTGATGAGTCCGTGAGGACG-AAACTTCCTGTTAGGATCCTGATGAGTCCGTGAGG-ACGAAACTGGCTCGCTATGTTCTGATGAGTCCGTG-AGGACGAAACACCCAA Rz-ψ (single Anti-HIVψ) (SEQ ID NO:6) GTCAAAAATTGGCGCTGATGAGTCCGTGA-GGACGAAACTCACCAGTCGCCG.

The cleavage of HIV RNA by ribozymes is a potentially useful approach. Therapeutically, it has several important properties—
  i) specificity,
  ii) the ability to target a relatively large number of potential sites,
  iii) lack of toxicity to cells,
  iv) turnover of the ribozyme molecule,
  v) variety of applicable delivery methods and
  vi) potential for a variety of methods of production: a) chemical synthesis (as it is a short molecule), b) biochemical production by in vitro transcription and c) promoter driven in vivo production from integrated constructs.

The present invention utilizes anti-packaging site (Psi) ribozymes to inhibit HIV replication. This activity would act at levels A, E, F and G. Cutting at this site can have inhibitory effects on: i) the entry of the virus into target cells ii) production of viral RNA iii) the translation of viral mRNA into viral proteins and iv) the packaging of viral genomic RNA into virions.

PSI PACKAGING SEQUENCE

The Psi packaging sequence is a cis-acting viral genomic sequence which is necessary for the specific encapsidation of viral RNA into virions (Aronoff et al., 1991). It has been shown that packaging of RNA into virus particles exhibits high specificity and this appears to be imparted by the Psi site. The location of the Psi packaging site for both Mo-MLV and HIV-1 was identified by functional deletion, that is removing certain sequences and observing whether the process of packaging of viral RNA continued. The sequence has been shown to be within the 5' untranslated region of the retrovirus and to be absent in RNAs which are not packaged. In terms of the present invention, we have deduced that, in order for the RNA to be easily recognized as one to be packaged, the packaging sequence must be exposed, accessible and able to be recognized. Studies of both the Mo-MLV and the HIV-1 packaging signal have indicated that in each case there is a conserved stable secondary structure (Alford et al., 1992 and Harrison et al., 1992). In our view these features have made the Psi packaging site an attractive target for ribozyme action. A study using antisense to the retroviral packaging sequence has previously shown that the replication of Moloney murine leukemia virus (Mo-MLV) can be inhibited in transgenic animals by interference with the Psi sequence (Han et al., 1991).

MOLONEY MURINE LEUKEMIA VIRUS (Mo-MLV) AND HUMAN IMMUNODEFICIENCY VIRUS (HIV-1)

Mo-MLV is a murine wild type retrovirus that does not carry an oncogene (FIG. 3) (Teich et al., 1985). It causes leukemia in mice with a long latency due to insertional mutagenesis. We have used Mo-MLV as a first step for assessing proof of principle for efficacy of anti-viral ribozymes. Mo-MLV is typical retrovirus in which replication proceeds along the lines outlined in FIG. 1 and packaging is effected via the Psi packaging site. In one embodiment of the present invention, anti-Mo-MLV ribozymes targeted to the Psi packaging site and cloned within an expression vector were tested for their ability to reduce virus production in tissue culture.

HIV-1, the active principle in Acquired Immune Deficiency Syndrome (AIDS) induces cell death in T lymphocytes (McCune, 1991; Levy, 1993). These cells are vital contributors to the immune response. In any potential anti-HIV approach it is essential to substantially reduce or inhibit viral replication before the immune system becomes crippled due to loss of these cells. There is currently no effective cure for AIDS. However, by reducing viral titer it is expected that progression of the disease will be slowed and may even be arrested. Development of anti-HIV-packaging sequence ribozymes appears to be a viable method for substantially inhibiting or even halting virus production.

Anti HIV-gag ribozymes have previously been developed which were shown to be able to reduce gag-RNA and p24 levels in cells expressing the ribozyme (Sarver et al., 1990).

Hammerhead ribozymes have been developed to cleave HIV-1 integrase RNA in *E. coli* to block translation of the integrase protein (Sioud et al., 1991). Studies have also shown that a ribozyme that also cleaves HIV-1 RNA in the U5, 5' untranslated region of HIV or tat can protect T cells from HIV-1 (Dropulic et al., 1992, Ojwang et al., 1992, Lo et al., 1992, and Weerasinghe et al., 1991).

In another preferred embodiment of the present invention, anti-HIV ribozymes targeted to the Psi packaging site and cloned within the same expression vector as for the anti-Mo-MLV construct. These constructs were also tested for their abilities to reduce virus production in tissue culture.

DELIVERY OF EXPRESSION CONSTRUCTS

The major means by which to introduce the expression constructs into target cells are transfection including electroporation, liposome mediated and retrovirally mediated gene transfer.

Definitions

As used herein, "Psi packaging site" refers to a region directly proximal to the 5' LTR which is involved in encapsidation of the viral RNA into virions.

As used herein, "complementary arms" are the sequences attached to the core hammerhead ribozyme which allow binding to a specific region of the target RNA.

As used herein, "ribozyme" may be of a hammerhead hairpin, hepatitis delta, RNase P, group I intron or group II intron, which are capable of cleaving target RNA. The hammerhead ribozyme is the subject of publication of Haseloff and Gerlach (Haseloff et al., 1988) and subsequent papers by a number of laboratories.

Description

This invention relates to the treatment of viral diseases, especially AIDS, in which the pathogenic agent has RNA as its genomic material and this RNA is packaged into virions. The approach is to inhibit replication of the virus by destroying the viral RNA at the Psi packaging site, the recognition sequence necessary for packaging of the viral genomic RNA. Cutting at this site has inhibitory effects on: i) the entry of the virus into target cells and, following integration of the provirus into the host genome, ii) production of viral RNA, iii) the translation of viral mRNA into viral proteins and iv) the packaging of viral genomic RNA into virions.

In one embodiment of the invention, certain expression constructs are provided, which comprise nucleotide sequences of interest. In a preferred expression construct, a ribozyme expression construct is provided which, when introduced into a cell, which may be a Mo-MLV or HIV-1 infected cell, is capable of directing transcription of RNA which, due to complementary arms surrounding the ribozyme, can bind to Mo-MLV or HIV-1 RNA. These complementary arms are short and it is the presence of ribozyme sequences which act to cut the RNA, thereby interfering with the action of the RNA molecule.

The invention has been tested in several ways. One set of experiments showed a direct correlation between ribozyme-mediated cleavage of the Mo-MLV viral Psi packaging sequence in vitro and the in vivo suppression of Mo-MLV replication. There were three main steps which were followed in order to reach this conclusion— i) Demonstration of ribozyme-mediated in vitro cleavage. ii) Transfection of constructs containing the ribozymes into Mo-MLV infected cells. iii) Various assays to show a) integration of constructs, b) ribozyme construct expression, c) effect of ribozyme construct expression on levels of virus replication.

For HIV, similar steps were followed— i) design and construction of ribozyme constructs, ii) transfection of ribozyme containing constructs into a human T lymphocyte cell line, iii) various assays to show a) integration of constructs, b) ribozyme construct expression c) effect of ribozyme construct expression on levels of virus replication.

The invention acts as a viral suppressant both to i) inhibit viral entry into a non-infected cell, by clipping the viral RNA as it enters the target cell and ii) to decrease levels of functional virus exiting the infected cell. In both cases, it acts to cut the viral RNA—at the entry point in the first case and at the exit point in the second. In the latter case, cutting decreases RNA levels by cutting both viral and mRNA. Cutting specifically at the Psi packaging site also serves to inhibit packaging of the viral RNA.

Several considerations were employed in order to choose a target for anti-viral ribozyme action. The criteria used for the present invention were— i) The target must be functionally important. ii) There must be a high degree of sequence conservation among the different HIV-1 isolates in the target region. iii) In the case of hammerhead ribozymes, the ribozyme target sequence such as GUC or GUA is preferably present in the sequence or the related triplets GUU, CUC etc. (Perriman, et al., 1992) iv) The target sequence should be readily accessible, for example it should lack extensive secondary structure (Rossi et al., 1992).

The Psi packaging site fitted the above criteria and was chosen as a target for cleavage by ribozymes. This site has: i) an essential function in the retroviral replication cycle, ii) relative accessibility, being a site on the RNA that must be recognized and accessible to other components in order for packaging to occur and iii) a conserved nature among different strains of the same virus.

It has been observed that in different strains of both Mo-MLV and HIV there is strong conservation of sequence and structure in the Psi packaging region of each virus. While there is no apparent conservation of structure or sequence between the packaging site of HIV and Mo-MLV, due to the identical function of the Psi site in each virus, it is reasonable to assume there must be similarities. The secondary structure of viral RNA was examined and sites on the Psi sequence were chosen that appeared to be accessible to ribozyme action. These were in the loop regions, that is single-stranded unpaired base regions of the RNA. Zuker's FOLDRNA program was used to locate non-base paired regions of the Psi packaging sequence. The ribozymes were designed to target these sites. The sites chosen also had a GUC base sequence present.

Figure 4:
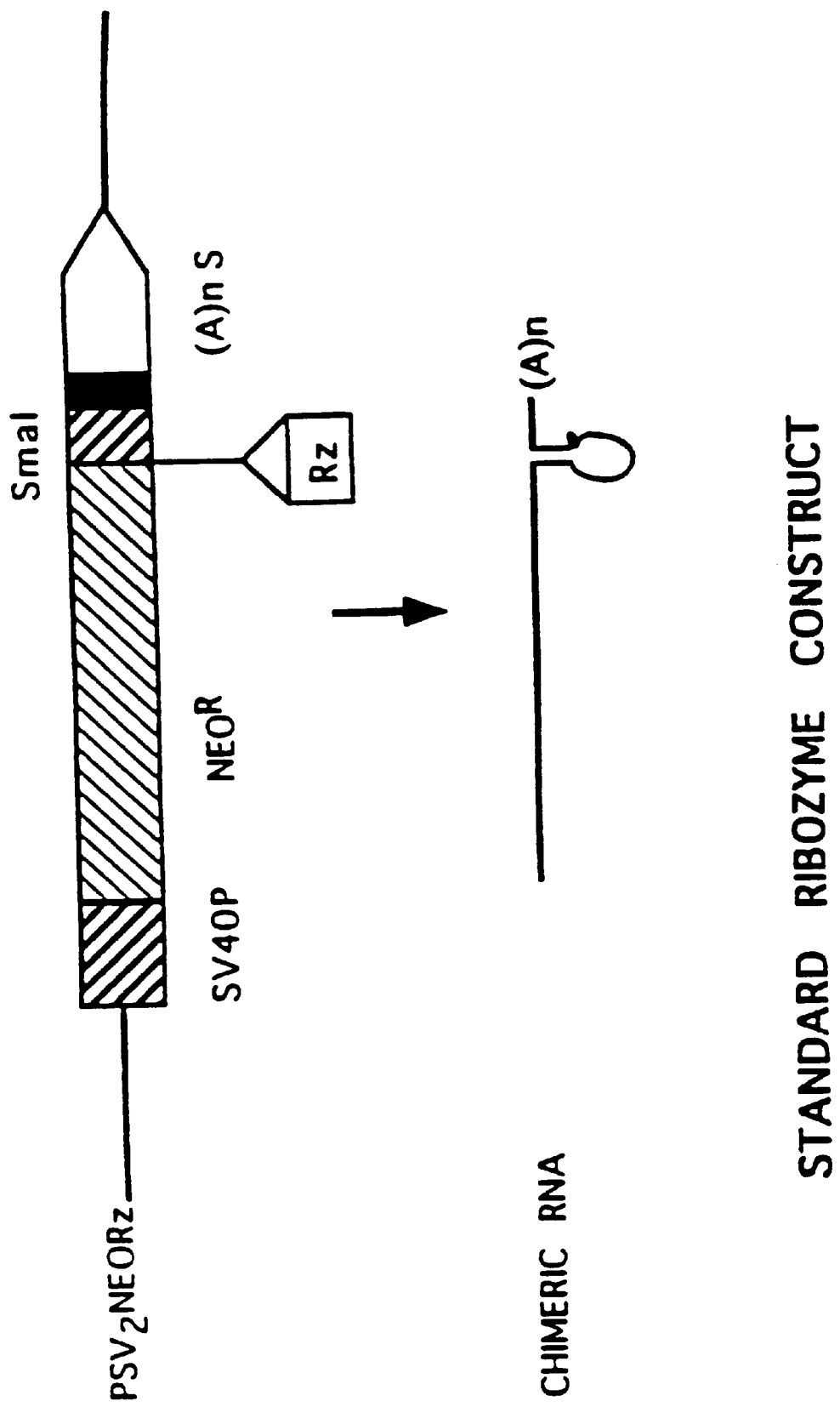
FIG. 4. Anti-MO-MLV and Anti-HIV packaging site constructs. The standard expression constructs were based on pSV2neo and consisted of the SV40 promoter upstream of the $neo^r$ gene with one of the designed ribozymes or an antisense sequence complementary to the Psi packaging sequence (anti-Psi) inserted into the Sma I site of $neo^r$.
Figure 5:
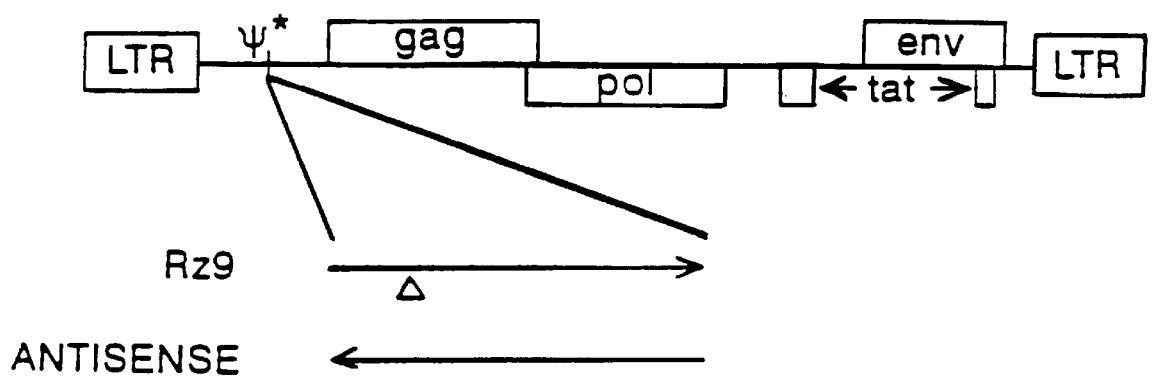
FIG. 5. HIV Packaging Site Targeted The figure shows a simplified view of the HIV genome with ribozyme 9 being targeted to a sequence within the Psi packaging site.

The constructs used in the present invention employed ribozymes inserted into the 3' untranslated region of neomycin resistance gene (neo$^r$). The basic construct is shown in FIG. 4. Such a construct allowed assessment of integration and expression. The former being determined by Southern analysis, the latter by cellular resistance to G418 toxicity and by RNAse protection assay. A further advantage of the design employed was that the chimeric RNA with a small ribozyme sequence in the 3' end of a larger neo$^r$ gene messenger appeared to act to keep the ribozymes stable within the cells. The latter is an extremely important point as without stability the effect of ribozymes will be minimal.

DISCUSSION

The invention provides the basis for a process by which ribozymes could be used to protect animals, including humans, from diseases caused by retroviruses. The basic principle of the invention is to incorporate, within a larger gene, ribozymes against the packaging site of the target retrovirus. The carrier gene may either be selectable (as in the present case) or non-selectable. Expression of the larger carrier gene provides a more stable chimeric ribozyme RNA molecule. The DNA construct is transfected into either a naive cell population to protect the cells or can be introduced into a virally-infected cell population to reduce viral titre. In a further embodiment, the ribozyme expression construct can also be introduced by retrovirally mediated gene transfer to increase the efficiency of introduction. A third embodiment of this invention is a retrovirus which carries an anti-packaging site ribozyme. If the retroviral vector is an MoMLV based, then the ribozyme targeted to the packaging site of HIV will not cleave the MoMLV packaging site due to sequence divergence for the two retroviruses Therapeutically, the application could involve introduction to the constructs into T lymphocytes ex vivo or into hematopoietic stem cells ex vivo. One preferred approach would be to incorporate the ribozyme constructs into lymphocytes or stem cells via a retroviral vector such as amphotropic Mo-MLV. Hematopoietic progenitor and true stem cells are promising targets for gene therapy because they are present in the bone marrow or can be mobilized into the peripheral blood. Progenitor cells may give rise to both myeloid and lymphoid cells, true stem cells giving rise to cells of all cellular lineages. Therapy could involve irradiation to destroy the HIV infected hematopoietic system and the stem cells containing the ribozyme would then be injected into the patient. As a result the patient's cells could be rendered resistant to HIV.

The invention is also directed to transfer vectors comprised of RNA or DNA or a combination thereof containing a nucleotide sequence which on transcription gives rise to the compounds described above. The transfer vector may be the HIV long terminal repeat, an adenovirus associated transfer vector, an SV40 promoter, Mo-MLV, or an amphotropic retrovirus vector. The transfer vector may further comprise a sequence directing the oligonucleotide compound to a particular organ or cell in vivo or a particular region within the cell. Examples of localizing to a particular region of a cell include the use of the packaging signal (Sullenger et al. 1993). The invention is also directed to compositions containing the compounds or transfer vectors described above in a suitable carrier. The carrier may be a pharmaceutically, veterinarially, or agriculturally acceptable carrier or excipient. The composition may further comprise a TAR decoy, polyTAR or a RRE decoy.

For production of the DNA sequences of the present invention in prokaryotic or eukaryotic hosts, the promoter sequences of the present invention may be either prokaryotic, eukaryotic or viral. Suitable promoters are inducible, repressible, or, more preferably, constitutive. Examples of suitable prokaryotic promoters include promoters capable of recognizing the T4 polymerases (Malik, S. et al., *J. Molec. Biol.* 195:471–480 (1987) Hu, M. et al., *Gene* 42:21–30 (1986), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)); the $P_R$ and $P_L$ promoters of bacteriophage lambda (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp. recA, heat shock, and lacZ promoters of *E. coli.*; the int promoter of bacteriophage lambda; the bla promoter of the β-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D. et al. *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981) and the yeast ga14 gene promoter (Johnston, S. A., et al. *Proc. Natl. Acad. Sci.* (USA) 79:6971–6975 (1982); Silver, P. A., et al., *Proc. Natl. Acad. Sci.* (USA) 81:5951–5955 (1984)).

For preparation of vectors for use in inhibiting retrovirus infection, in susceptible eukaryotic cells or in whole animals, eukaryotic promoters must be utilized, as described above. Preferred promoters and additional regulatory elements, such as polyadenylation signals, are those which should yield maximum expression in the cell type which the retrovirus to be inhibited infects. Thus, for example, HIV-1, HIV-2, HTLV-1 and HTLV-2, as well as the Moloney murine leukemia virus, all infect lymphoid cells, and in order to efficiently express a ribozyme construct alone or in combination with an antisense RNA complementary to the packaging sequence of one (or more) of these viruses, a transcriptional control unit (promoter and polyadenylation signal) are selected which provide efficient expression in hematopoietic, particularly lymphoid cells (or tissues). As exemplified below, preferred promoters are the cytomegalovirus immediate early promoter (32), optionally used in conjunction with the growth hormone polyadenylation signals (33), and the promoter of the Moloney-MuLV LTR, for use with a lymphotropic retrovirus. A desirable feature of the Moloney-MuLV LTR promoter is that it has the same tissue tropism as does the retrovirus. The CMV promoter is expressed in lymphocytes. Other promoters include VA1 and tRNA promoters. The metallothionein promoter has the advantage of inducibility. The SV40 early promoter exhibits high level expression in vitro in bone marrow cells.

The invention is also directed to methods for producing the compounds which comprise the steps of: (a) ligating into a transfer vector comprised of DNA, RNA or a combination thereof a nucleotide sequence corresponding to the compound; (b) transcribing the nucleotide sequence of step (a) with an RNA polymerase; and (c) recovering the compound.

The invention is also directed to prokaryotic or eukaryotic host cells comprising a nucleotide sequence which is, or on transcription gives rise to the compounds described above. The cell may be an animal cell, a hematopoietic stem cell which gives rise to progenitor cells, more mature, and fully mature cells of all the hematopoietic cell lineages, a progenitor cell which gives rise to mature cells of all the hematopoietic cell lineages, a committed progenitor cell above to protect hematopoietic stem cells, progenitor cells, committed progenitor cells, T lymphocyte progenitor cells, immature T lymphocytes, mature T lymphocytes, myeloid progenitor cells, or monocyte/macrophage cells. Further, method to suppress/treat or protect against HIV in a patient which comprises the introduction of the transfer vector above into hematopoietic cells thereby rendering the cells resistant to HIV so as to thereby suppress/treat or protect against HIV. The introduction is ex vivo and the cells are autologous or heterologous cells with or without myeloablation. In one embodiment of the present invention, three single and one multiple hammerhead ribozymes were designed to target different sites within the Mo-MLV Psi packaging site and one ribozyme was designed to target a site within the HIV Psi packaging site (See FIG. 2). Mo-MLV was chosen as an example of a retrovirus in which to determine principles of action. These principles would apply to other retroviruses including HIV. Testing was also carried out for HIV-1.

In the present invention the nonhuman animal and progeny thereof contain at least some cells that express or retain the non-naturally occuring oligonucleotide compound. The transgenic nonhuman animal all of whose germ and somatic cells contain the non-naturally occuring oligonucleotide compound in expressible form introduced into said animal, or an ancestor thereof, at an embryonic stage as described in U.S. Pat. Nos. 4,736,866, 5,175,383, 5,175,384, or 5,175,385. See also (Van Brunt, 1988; Hammer, 1985; Gordon et al., 1987; Pittius et al., 1988; Simons et al. 1987; Simons et al., 1988).

The invention also includes a process for rendering cells resistant to viral infection which comprises treating the cells with the non-naturally occuring oligonucleotide compound described above. Preferably, the treatment is ex vivo. In addition as used herein the terms antisense and ribozymes also include compounds with modified nucleotides, deoxynucleotides, peptide nucleic acids, etc. These would be used for ex vivo treatment or topical treatment.

An effective amount of the non-naturally occuring oligonucleotide compound of the present invention would generally comprise from about 1 nM to about 1 mM concentration in a dosage form, such as a cream for topical application, a sterile injectable composition, or other composition for parenteral administration. In respect of topical formulations, it is generally preferred that between about 50 $\mu$M to about 500 $\mu$M non-naturally occuring oligonucleotide compound be employed. Compounds comprising nucleotide derivatives, which derivatives may involve chemically modified groups, such as phosphorothioate or methyl phosphonate derivatives may be active in nanomolar concentrations. Such concentrations may also be employed to avoid toxicity.

Therapeutic strategies involving treatment of disease employing compounds of this invention are generally the same as those involved with antisense approaches, such as described in the anti-sense bibliography of (Chrisley, 1991). Particularly, concentrations of compounds utilized, methods and modes of administration, and formulations involved may be the same as those employed for antisense applications.

An "effective amount" as used herein refers to that amount which provides a desired effect in a mammal having a given condition and administration regimen. Compositions comprising effective amounts together with suitable diluents, preservatives, solubilizers, emulsifiers, adjuvants and/or carriers useful for therapy. Such compositions are liquids or lyophilized or otherwise dried formulations and include diluents of various buffer content (e.g., Tris-HCL, acetate phosphate), pH and ionic strength, additives such as albumin or gelatin to prevent absorption to surfaces, detergents (e.g., Tween 20, Tween 80, Pluronic F68, bile acid salts), solubilizing agents (e.g., Thimerosal, benzyl alcohol), bulking substances or tonicity modifiers (e.g., lactose, mannitol), covalent attachment of polymers such as polyethylene glycol to the non-naturally occuring oligonucleotide compound, complexation with metal ions, or incorporation of the material into or onto particulate preparations of polymeric compounds such as polylactic acid, polyglycolic acid, polyvinyl pyrrolidone, etc. or into liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of the oligonucleotide. Other ingredients optionally may be added such as antioxidants, e.g., ascorbic acid; low molecular weight (less than about ten residues) polypeptides, i.e., polyarginine or tripeptides; proteins, such as serum albumin, gelatin, or immunoglobulins; amino acids; such as glycine, glutamine acid, aspartic acid, or arginine; chelating agents such as EDTA; and sugar alcohols such as mannitol or sorbitol. Possible sustained release compositions include formulation of lipophilic depots (e.g., fatty acids, waxes, oils). Also comprehended by the invention are particulate compositions coated with polymers (e.g., polyoxamers or polyoxamines) and non-naturally occuring oligonucleotide compound coupled to antibodies directed against tissue-specific receptors, ligands or antigens or coupled to ligands of tissue-specific receptors. Further, specific nucleotide sequences may be added to target the non-naturally occuring oligonucleotide compound of this invention to the nucleus, plastid, cytoplasm or to specific types of cells. Other embodiments of the compositions of the invention incorporate particulate forms protective coatings, protease inhibitors or permeation enhancers for various routes of administration, including parenteral, pulmonary, nasal and oral.

Suitable topical formulations include gels, creams, solutions, emulsions, carbohydrate polymers, biodegradable matrices thereof; vapors, mists, aerosols, or other inhalants. The non-naturally occuring oligonucleotide compound may be encapsulated in a wafer, wax, film or solid carrier, including chewing gums. Permeation enhancers to aid in transport to movement across the epithelial layer are also known in the art and include, but are not limited to, dimethyl sulfoxide and glycols.

Ribonucleotide and deoxyribonucleotide derivatives or modifications are well known in the art, and are compatible with commercially available DNA synthesizers. (See Saenger, 1984, particularly pages 159–200). Nucleotides comprise a base, sugar and a monophosphate group. Accordingly, nucleotide derivatives, substitutions, or modifications may be made at the level of the base, sugar, or monophosphate.

A large number of modified bases are found in nature, and a wide range of modified bases have been synthetically produced (Saenger, 1984; and CRC Handbook of Biochemistry). Suitable bases would include inosine, 5'-methylcytosine, 5'-bromouracil, xanthine, hypoxanthine and other such bases. For example, amino groups and ring nitrogens may be alkylated, such as alkylation of ring nitrogen atoms or carbon atoms such as $N^1$ and $N^7$ of guanine and $C^5$ of cytosine; substitution of keto by thioketo groups; saturation of carbon=carbon double bonds, and introduction of a C-glycosyl link in pseudouridine. Examples of thioketo derivatives are 6-mercaptopurine and 6-mercaptoguanine.

Bases may be substituted with various groups, such as halogen, hydroxy, amine, alkyl, azido, nitro, phenyl and the like. Bases may be substituted with other chemical species, such as an amino-acid side chain or linkers which may or may not incorporate other chemical entities, e.g. acidic or basic groups. For example, guanine ($G_3$) may be substituted with tyrosine, and cytosine (C1) or adenine (A11) similarly substituted with histidine.

The sugar moiety of the nucleotide may also be modified according to well known methods in the art (Saenger, 1984). This invention embraces various modifications to the sugar moiety of nucleotides as long as such modifications do not abolish cleavage activity of the compound. Examples of modified sugars include replacement of secondary hydroxyl groups with halogen, amino or azido groups; 2'-methylation; conformational variants such as the $O_2$'-hydroxyl being cis-oriented to the glycosyl $C_1$. —N link to provide arabinonucleosides, and conformational isomers at carbon $C_1$, to give α-nucleosides, and the like. Further, non ribose sugars may be used such as hexoses such as glucose, pentoses such as arabinose.

The phosphate moiety of nucleosides is also subject to derivatisation or modifications, which are well known in the art. For example, replacement of oxygen with nitrogen, sulphur or carbon derivatives to respectively give phosphoramidates, phosphorothioates, phosphodithiolates, and phosphonates. Substitutions of oxygen with nitrogen, sulphur of carbon derivatives may be made in bridging or non bridging positions. It has been well established from work involving antisense oligonucleotides that phosphodiester and phosphorothioate derivatives may efficiently enter cells (particularly when of short length), possibly due to association with a cellular receptor. Methylphosphonates are probably readily taken up by cells by virtue of their electrical neutrality.

The phosphate moiety may be completely replaced with peptide nucleic acids (see Hanvey et al., 1992; Nielson, 1991; and Egholm, 1992). Other replacements are well-known to those skilled in the art for example siloxane bridges, carbonate bridges, acetamidate bridges, carbamate bridges, thioether bridges, etc. (Uhlmann and Peymann, 1990).

The following examples are for illustration of the claimed invention. This invention is illustrated in the Experimental Detail sections which follow. These sections are set forth to aid in an understanding of the invention but are not intended to, and should not be construed to, limit in any way the invention as set forth in the claims which follow thereafter.

EXAMPLE 1

In vitro Ribozyme-Catalyzed Cleavage of Mo-MLV Psi Packaging Sequences

In order to show that the target sites were indeed cleavable, in vitro cleavage reactions were performed prior to ribozyme testing in cell culture.

Figure 2:
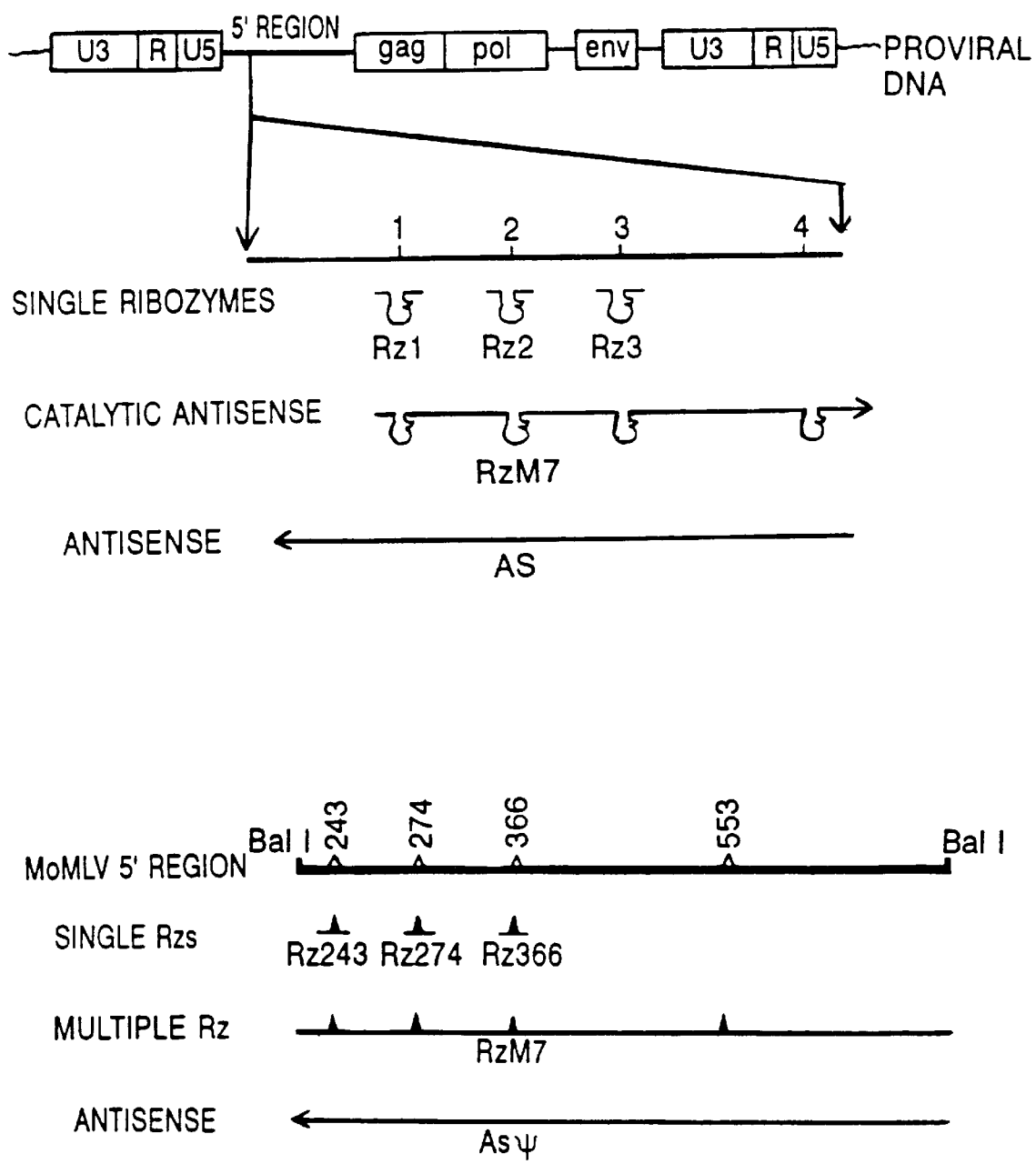
FIG. 2. Ribozyme targeting sites within the Mo-MLV Psi packaging region. Mo-MLV 5' region represents a BalI/BalI fragment (nt 212 to nt 747) of pMLV-1 (defined in the text). Arrows indicate the ribozyme targeting sites all of which were GUC residues.

Four sites were chosen in the Mo-MLV packaging region according to the presence of GUC bases and the potential accessibility of the sites within the proposed RNA secondary structure derived from Zuker's FOLDRNA program (Zuker et al., 1981). The sites were designated 243, 274, 366 and 553, based on their nucleotide distance from the 5' end of the viral transcript (FIG. 2). These nucleotide positions are as described in RNA Tumor Viruses (Coffin, 1985). Two types of ribozyme were designed: three single ribozymes targeted individually to sites 243, 274 and 366 with arms of length 12 nucleotides and one multiple ribozyme targeted to all four sites with intervening arms of the length of sequences between each of the target sites. The sites and overall design are shown in FIG. 2.

The single ribozymes were constructed by cloning an artificial double stranded insert with overhanging PstI and EcoRI ends into pGEM3Zf(+). The resulting plasmids were pGEM243, pGEM274 and pGEM366. The multiple ribozyme was constructed by a variation of standard in vitro mutagenesis protocols (Warrilow et al., 1992). This plasmid was termed pGEM-M7. Successful cloning and sequence integrity were confirmed by DNA sequencing.

The Psi packaging sequence, in the Bal I-Bal I fragment of Mo-MLV derived from pMLV-1 (Coffin, 1985), was cloned into the pGEM3Zf(+) vector and transcribed as a substrate for in vitro ribozyme cleavage. Run-off transcription mixture (50 µl) for generating either ribozymes or substrate contained 1 µg linearized proteinase K treated DNA template, 30 mM dithiothreitol, 400 uM of each rNTPs, 40 mM Tris-Cl, pH 8.0, 2 mM spermidine, 6 mM $MgCl_2$, 50 mM NaCl, 1 µl of [$\alpha$-$^{32}$P]-UTP (400–800 Ci/mmole, 10 mCi/ml), 1 unit RNasin and 10 units T7 or SP6 RNA polymerase (Stratagene). After 1 h incubation at 37° C., 10 units of RNase-free DNase (Promega) were added, and the mixture was incubated for 15 min at 37° C. After phenol-chloroform extraction, RNA transcripts were precipitated by adding 0.1 volume of 3 M sodium acetate and 2.5 volume of ethanol. For cleavage reactions, the ribozyme and substrate (1:1 molar ratio) were pre-incubated at 80° C. for 2 minutes, followed by 30 minutes of incubation at 37° C. in the presence of 50 mM Tris-Cl, pH 7.5 and 10 mM $MgCl_2$. Reactions were stopped by the addition of an equal volume of stop mix (8 M urea, 50 mM EDTA, 0.05% bromphenol blue and 0.05% xylene cyanol) and analyzed on a denaturing 6% polyacrylamide gel containing 8 M urea, followed by autoradiography.

Engineered ribozymes targeted to different sites of the Mo-MLV proviral packaging sequence were shown to cleave target RNA in vitro at the chosen sites.

Figure 3:
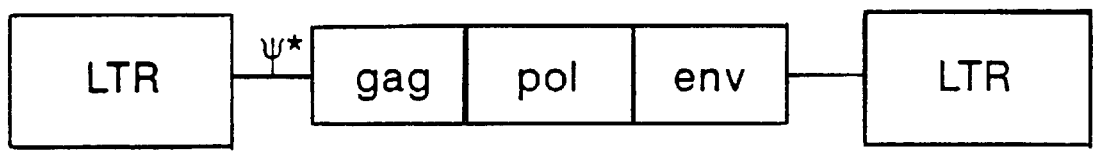
FIG. 3. Genome of Moloney murine leukemia virus The genome of MoMLV consists of the replicative genes gag, pol and env and the 5' and 3' long terminal repeats (LTRs). The Psi packaging site is necessary for packaging of the viral RNA into the virion.
Figure 6:
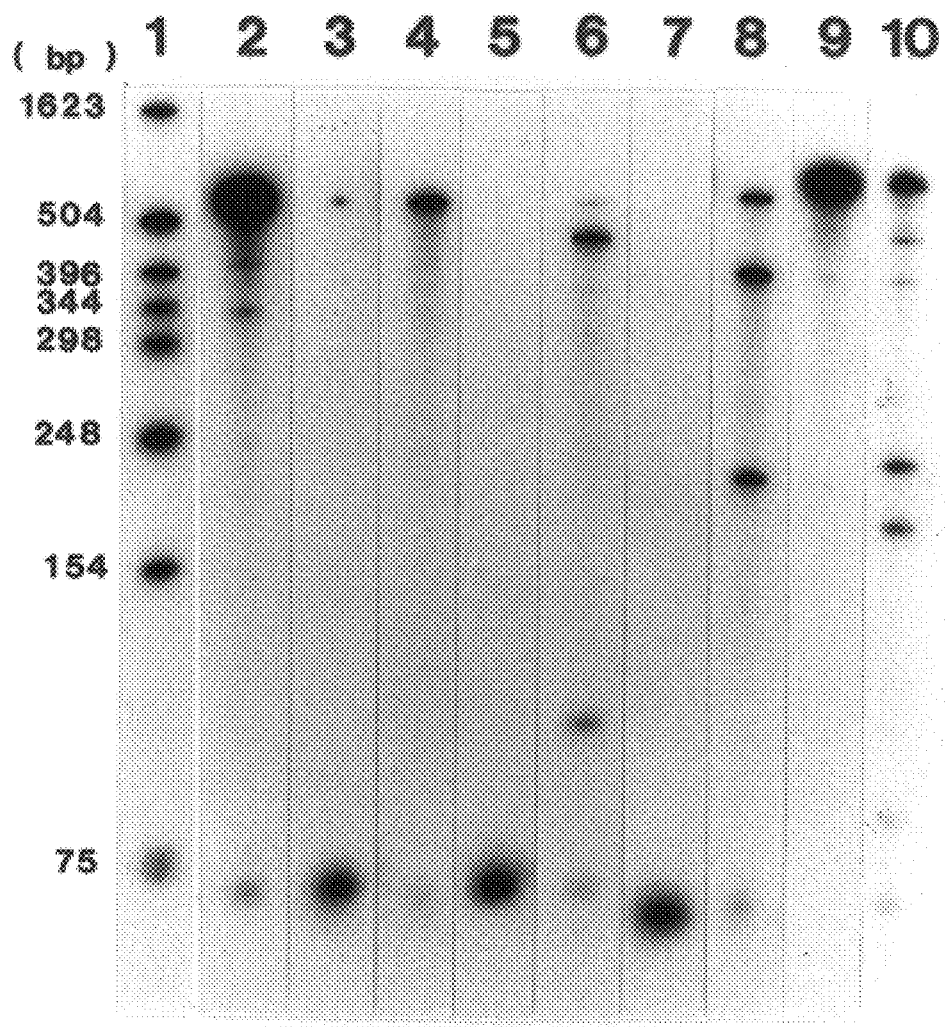
FIG. 6. In vitro cleavage of in vitro generated Mo-MLV packaging region RNA by ribozymes. Lane 1 is pBR322 marker DNA digested with HinfI. Lane 2 is the approximately 550 kb substrate. Lanes 3, 5, 7 and 9 were the in vitro generated Rz243, Rz274, Rz366 and Rz-M7 alone. The following ribozymes were added to target substrate RNA: lane 4, Rz243; lane 6, Rz274; lane 8, Rz366; lane 10, Rz-M7. The cleavage reactions were carried out at 37° C. for 30 min in 10 mM $MgCl_2$, 50 mM Tris.Cl, pH 7.5 after the samples were heated at 80° C. for 2 min in 10 mM Tris.Cl, pH 7.5.

For the majority of the ribozyme constructs, incubation of a $^{32}$P-labelled Psi transcript with $^{32}$P-labelled ribozyme RNA in an approximately equimolar amount led to efficient cleavage of the substrate under mild physical conditions (37° C., 10 mM $MgCl_2$ and 50 mM Tris.Cl, pH 7.5). Representative examples of these digestions are shown in FIG. 6. The size of the cleaved Psi fragments produced by Rz274 and Rz366 were consistent with the location of predicted sites for cleavage, resulting in bands of 62 nt plus 473 nt and 154 nt plus 381 nt respectively. The multiple ribozyme (Rz-M7) produced four fragments (50 nt, 92 nt, 187 nt and 240 nt) as predicted as well as several partially cleaved fragments (FIG. 3). For Rz243, there was no visible cleavage at 37° C. and weak cleavage, yielding appropriate size fragments, at 50° C. (data not shown). With the exception of ribozyme 243, these results indicated efficient site-specific ribozyme mediated cleavage.

EXAMPLE 2
Anti-Mo-MLV Packaging Site (Psi) Constructs

Following demonstration of efficient in vitro cleavage, the engineered ribozymes as well as a long antisense sequence complementary to the Psi packaging region were cloned into the 3' untranslated region of the $neo^r$ gene coupled to the simian virus 40 (SV40) early promoter (FIG. 4). $neo^r$ is a prokaryotic gene which codes for an enzyme that phosphorylates and, thereby inactivates neomycin or the neomycin analogue G418. The latter is toxic for mammalian cells and the expression of an exogenous $neo^r$ gene permits cell survival. This construct with the SV40 promoter coupled to the $neo^r$ gene is within a mammalian expression vector, pSV2neo and is shown diagrammatically in FIG. 4.

The ribozyme inserts and an antisense control were cloned into a SmaI site in the 3' untranslated region of $neo^r$ by blunt-ended ligation. The resultant vectors were termed pSV243, pSV274, pSV366, pSVM7 and pSVas Psi (the antisense construct) respectively.

EXAMPLE 3
Transfection of Constructs into 3T3-Mo-MLV Producing Cell Lines

Figure 7:
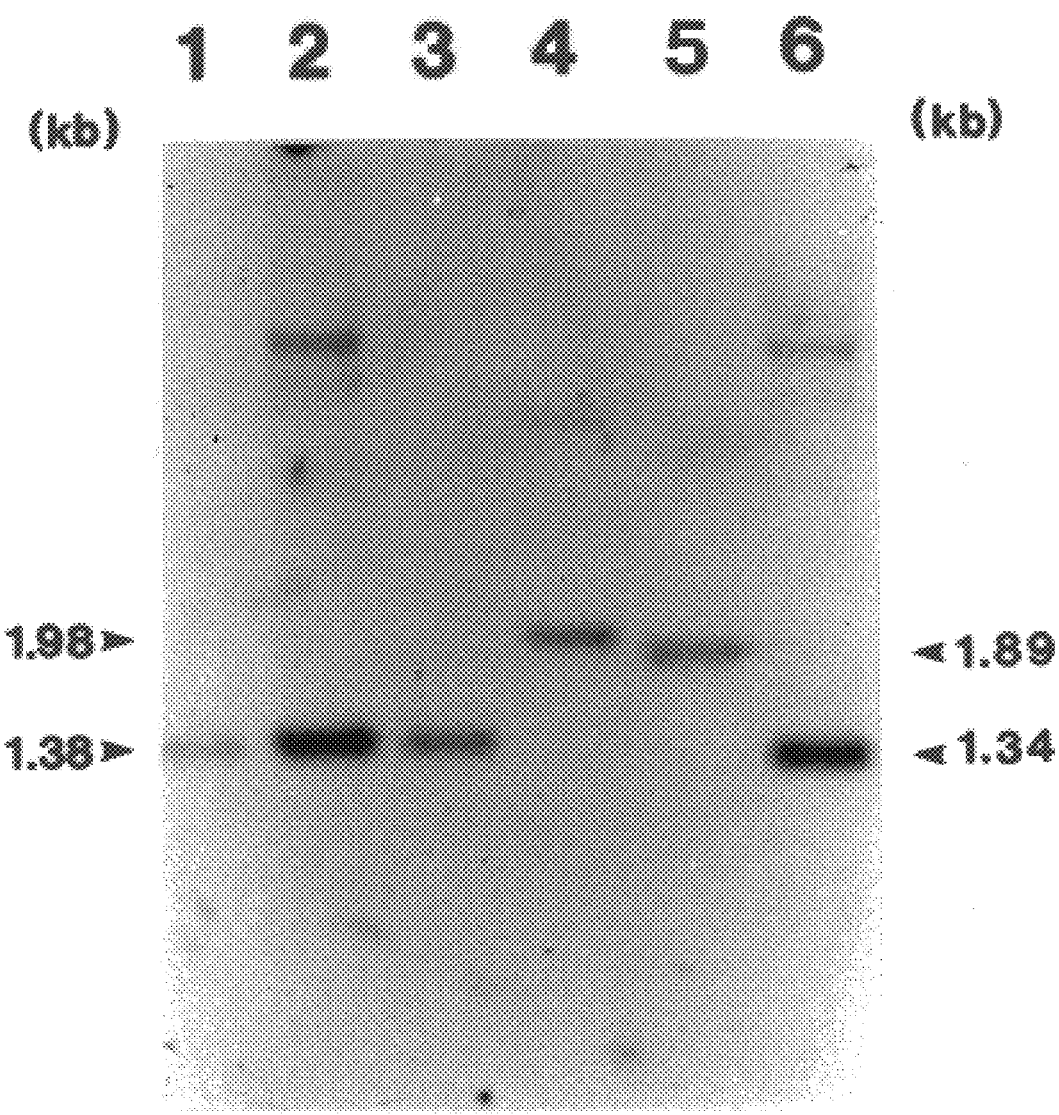
FIG. 7. Southern hybridization of DNA from the ribozyme or antisense construct-transfected cell lines. Genomic DNA (10 μg) from 3T3-Mo-MLV cells transfected with the various constructs: lane 1, pSV243; lane 2, pSV274; lane 3, pSV366; lane 4, pSV-M7; lane 5, pSVAs-Psi; and lane 6, pSV2neo vector alone were digested with HindIII/NruI, separated on a 0.6% agarose gel, blotted onto nitrocellulose filter and hybridized with the $^{32}$P-labelled $neo^r$ gene probe. Arrowheads indicate the predicted size of the $neo^r$ gene alone (1.34 kb) and the $neo^r$ gene plus the single ribozymes (1.38 kb), plus a multiple Rz (1.98 kb), or plus antisense (1.89 kb).

The various pSV2neo based constructs were transfected into 3T3-Mo-MLV cells using a calcium phosphate transfection protocol (Chen et al., 1987). Positive colonies were those that formed after 9–12 days in the presence of 500 μg/ml of G418. For each construct, 4–7 colonies were isolated using cloning cylinders. These colonies were grown, stored in liquid $N_2$ and then used for further assays. After 10–14 days selection in 500 μg/ml of G418, several stable clonal cell lines for each construct were established. To confirm the integration of transfected DNA expression constructs, genomic DNA was prepared from certain of the transfected cell lines and Southern analysis performed. The restriction enzymes HindIII and NruI were used to digest genomic DNA to generate a fragment containing the $neo^r$ gene plus inserts (ribozymes or antisense). Presence of the construct could then be determined by using a $neo^r$ specific probe. From the Southern analysis shown in FIG. 7, it is clear that the cells transfected with both ribozyme and antisense constructs and selected in G418 contain the $neo^r$ gene plus appropriate ribozyme or antisense sequences. The size of the HindIII-NruI fragments hybridizing with the $neo^r$ probe were found to be the predicted size in each case, namely 1.3 kb for $neo^r$ gene alone; 1.38 kb for $neo^r$ plus the single ribozyme; 1.98 kb for $neo^r$ plus a multiple ribozyme; 1.89 kb for $neo^r$ plus the antisense sequence.

Figure 8:
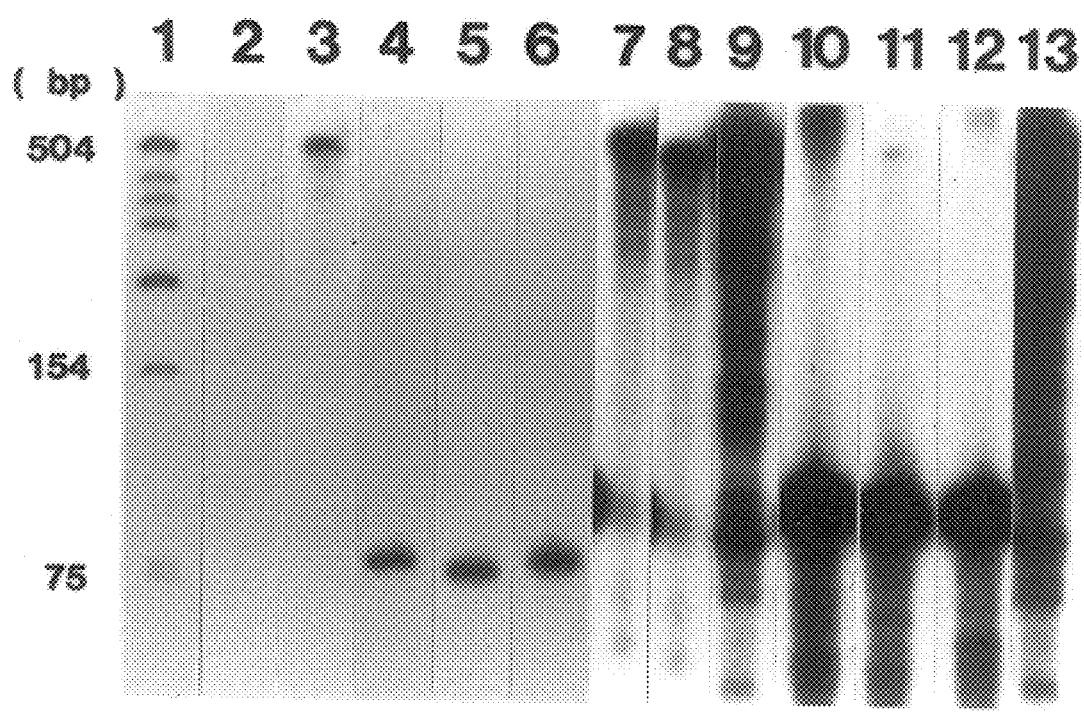
FIG. 8. RNase protection analysis to study ribozyme/antisense constructs expression. 20 μg total RNA from a series of transfected cells was analyzed for expression of the ribozymes or antisense constructs using $^{32}$P-labelled riboprobes. Lane 1, size marker end labelled DNA fragments of pBR322 digested with HinfI; lane 2, riboprobe of RzM7 hybridized with yeast RNA and digested with RNase; lane 3, riboprobe of RzM7 hybridized with yeast RNA, followed by no RNase digestion; lanes 4–8, riboprobes of Rz243, Rz274, Rz366, RzM7 and As-Psi hybridized with RNA from pSV243, pSV274, pSV366, pSV-M7 and pSVAs-Psi transfected cells respectively, and digested with RNase; lanes 9–13, riboprobes of RzM7, Rz243, Rz274, Rz366 and As-Psi only. One clone for each construct which showed the best suppression of Mo-MLV replication was used in the assay.

Expression of the ribozyme or antisense constructs was predicted due to G418 resistance in the positive transfectants. This was further examined in the transfected cells using RNase protection assay. Total RNA was extracted using a guanidium thiocyanate procedure from certain of the cell lines, 20 μg of total RNA was then hybridized with the corresponding $^{32}$P-labelled riboprobes ($5 \times 10^4$ cpm) in a solution containing 80% deionized formamide, 100 mM sodium citrate pH 6.4, 300 mM sodium acetate pH 6.4, 1 mM EDTA, followed by RNase digestion of the hybridized RNAs (5 μg/ml RNase A and 10 units/ml RNaseT1). If the ribozyme was not expressed, then the complementary riboprobe would be unable to bind. The RNA would then remain single stranded and would be totally digested by RNase. The reaction mixture was then separated by electrophoresis. As shown in FIG. 8, the assays revealed that all the ribozymes and antisense constructs were expressed as expected. The protected fragments are 65 bp (single ribozymes); 588 bp multiple ribozymes and 524 bp (antisense).

EXAMPLE 4
Ability of Constructs to Suppress Mo-MLV Replication

After the establishment of stable 3T3 Mo-MLV clonal cell lines transfected with different constructs, XC plaque assay was employed to evaluate the level of Mo-MLV replication. XC assay is a syncitial plaque assay for Mo-MLV, which is based on the observation that Mo-MLV-producing cells can cause fusion of XC cells. Mo-MLV was titrated as described in (Gautsch et al., 1976) except that 8 μg/ml polybrene (Sigma) was present during infection to enhance viral binding to the target cells. Supernatants from the culture of the different Mo-MLV-producing cell lines were added to uninfected mouse NIH3T3 cells which were pre-treated with 8 μg/ml polybrene for 1 hr prior to infection. After 20 hr incubation in growth medium, the infected NIH3T3 cells were co-cultivated with XC cells in a $2 \times 2$ mm$^2$ grided plate for 3 to 4 days. The plates were then fixed with methanol, stained with 1% methylene blue plus 0.1% Gentian violet and scanned for syncitium plaques by microscopy. To ensure that the assays were performed within the linear portion of the dose-response curve, $3.5 \times 10^5$ cells per plate were infected with two-fold serial dilutions of the virus and passaged 24 hr later to a mixed culture with XC cells. The results in Table 1 were from three independent experiments. 74% to 77% inhibition of syncitium plaque formation were observed from the cells containing Rz274, Rz366, Rz-M7 and As-Psi in relation to pSV2neo vector-containing cells, whereas no apparent inhibition was shown for Rz243-containing cells.

These data are consistent with in vitro cleavage results (FIG. 6) in which Rz243 did not appear to efficiently cleave the substrate under the conditions used.

Figure 9:
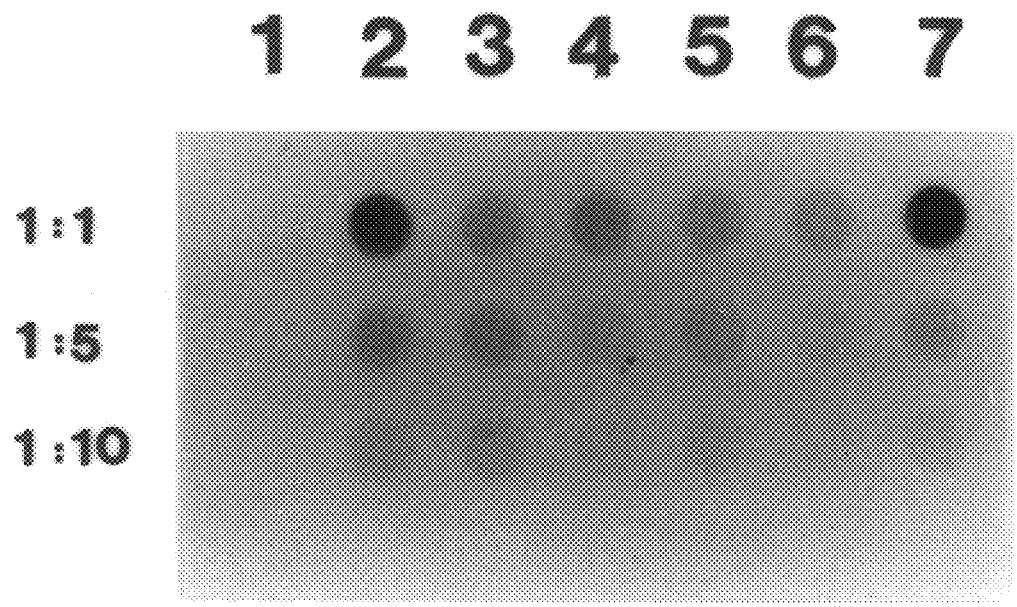
FIG. 9. Autoradiograph of a dot blot of viral RNA derived from different Mo-MLV-producing 3T3 cells. Viral RNA preparations at 1:1, 1:5 and 1:10 dilutions were probed with a $^{32}$P-labelled riboprobe complementary to Mo-MLV Psi packaging region as described previously. Lane 1, yeast RNA; lanes 2–7, RNA from supernatants of 3T3-Mo-MLV cells transfected with pSV243, pSV274, pSV366, pSV-M7, pSVAsPsi and pSV2neo. It can be seen that viral RNA levels are lowered by the ribozymes effective in cleaving RNA target molecules in vitro and by the antisense.

These suppressive effects were confirmed using viral RNA dot-blotting in which 1 ml of supernatant from a 16 hr culture of NIH3T3 virus-producing cells was clarified by centrifuging (12,000 rpm, 10 min, 4° C.) in a microcentrifuge. Viral RNA was precipitated in 8% PEG 8000 and 0.5 M NaCl. After phenol-chloroform extraction, RNA was blotted onto positively charged nylon membrane (Zeta-Probe, Bio-Rad) in an alkali transfer solution (Reed et al., 1985). Hybridization was performed at 42° C. overnight in 50% formamide, 5×SSPE, 5×Denhardt's solution, 0.5% SDS, 100 mg/ml denatured herring sperm DNA and $^{32}$P-labelled riboprobe transcribed from T7 promoter of pGEM-Psi. Viral RNA was quantitated by dot scintillation counting. Viral RNA in the supernatants from the ribozyme or antisense-transfected 3T3-Mo-MLV cells was measured and compared with that in the supernatant from pSV2neo-transfected 3T3-Mo-MLV cells. As can be seen from FIG. 9 and Table 2 (except for Rz243-expressing cells), the amount of viral RNA produced from all the cell lines expressing ribozymes or antisense was substantially reduced by amounts similar to those seen by syncytia assay.

Following transfection of these ribozyme constructs into Mo-MLV infected cells, only those ribozymes which showed efficient in vitro cleavage exhibited the ability to suppress (approximately 70–80%) Mo-MLV replication in vivo. These results demonstrate a direct correlation between in vitro cleavage and in vivo ribozyme mediated virus suppression.

The previous experiments became the basis for further studies of ribozymes designed to target sites on the HIV Psi packaging sequence in order to reduce viral titre.

TABLE 1

Syncitium plaques induced by Mo-MLV released from transfected cells.

| Cell* | Syncitium plaques† | Inhibition (%) |
|---|---|---|
| Rz243 | 32 ± 12 | — |
| Rz274 | 7 ± 3 | 77 |
| Rz366 | 8 ± 1 | 74 |
| Rz-M7 | 7 ± 3 | 77 |
| As-Psi | 8 ± 2 | 74 |
| pSV2neo | 31 ± 1 | 0 |

*$10^{-2}$ dilution of the supernatant from Rz or As Construct-containing cells was used in infection of NIH3T3 cells.
†The number is a mean of the plaque counts from two clonal lines of each construct in three independent experiments. The numbers are presented as the mean ± standard error. Replicate plates receiving the same dilution of infected cells generally contained similar numbers of syncitial plaques.

TABLE 2

Degree of hybridization to viral RNA dot blots

| Sample | cpm × $10^{-3*}$ | Inhibition (%) |
|---|---|---|
| tRNA | 0.00 | — |
| Rz243 | 2.59 | 21 |
| Rz274 | 0.63 | 81 |
| Rz366 | 1.36 | 59 |
| RZ-M7 | 0.93 | 72 |
| As-ψ | 0.96 | 71 |
| pSV2neo | 3.30 | 0 |

*cpm counts were derived from two blots in 1:1 dilution row. The viral RNA dot blot assay was carried out as described in Materials and Methods. Following autoradiography, the filters corresponding to each dot were excised for liquid scintillation counting.

EXAMPLE 5
The Anti- HIV Packaging Site Construct

One GUA site was chosen in the HIV-1 (HIVSF2, Levy, 1984) Psi packaging region (nuc. 735 to nuc. 765 from 5' end of HIV genome) for ribozyme targeting. As for the previous constructs, the synthetic ribozyme insert was cloned into a Sma 1 site in the 3' untranslated region of the neo$^r$ gene of pSV2neo vector by blunt-ended ligation. Successful cloning and sequence integrity were confirmed by DNA sequencing. This construct was termed pSV-Rz-HIV-Psi. FIG. 4 shows a diagram of the construct.

EXAMPLE 6
Transfection of pSV-Rz-HIV-Psi Construct into T Lymphocytes

The anti-HIV packaging site construct, pSV-Rz-HIV-Psi, was electroporated into Sup T-1 cells, a human T lymphoma cell line. Exponentially growing cells were harvested and the number of viable cells counted by dye exclusion. The cells were washed with PBS and resuspended at a density of $1 \times 10^7$ viable cells/ml in RPMI media without FCS but containing 10 mM dextrose and 0.1 mM dithiothreitol. 0.4 ml of the cell suspension and 10 μg of pSV-Rz-HIV-Psi plasmid DNA were used per electroporation in 0.4 cm cuvettes (Bio-Rad). The cell and DNA mixture was subjected to a single pulse of 960 μF, 200 V from a Gene Pulser (Bio-Rad). After shocking, the cuvette was incubated for 10 minutes at room temperature, and the cells were then transferred to 10 ml of RPMI media with 10% FCS and placed into an incubator (5% $CO_2$, 37° C.). At 48 hours post electroporation, the cells were selected in medium supplemented with 800 μg/ml G418. 9–12 days later, positive colonies were isolated and grown as clonal isolates to be used in a HIV protection assay.

EXAMPLE 7
Assessment of Ability of Ribozyme Expression Constructs to Confer Protection against HIV Challenge Two assays, p24 antigen and syncytium formation, were performed to assess efficacy of the anti-HIV Psi ribozyme construct in cell culture. HIV-1 p24 antigen assay is an enzyme immunoassay, which uses a murine monoclonal antibody against HIV core antigen coated onto microwell strips. The HIV-1 syncytium assay is based on the observation that HIV-1 interacts with target T lymphocytes by causing fusion resulting in the formation of syncytia, large cells containing many nuclei. The clonal ribozyme-construct expressing cells, plus controls, were infected with HIV-1 (SF2) at m.o.i. of 0.1 to 1. After 2 hours, the cells were washed, and 10 ml of fresh media was added. Every 3–4 days, the number of both syncitia and viable cells were counted. For syncitia formation, approximately a two log higher dose was required in order to show the same result as in the control which did not include the ribozyme (Table 3). In addition, the presence of the ribozyme caused a delay in syncitia formation (Table 4).

Figure 10:
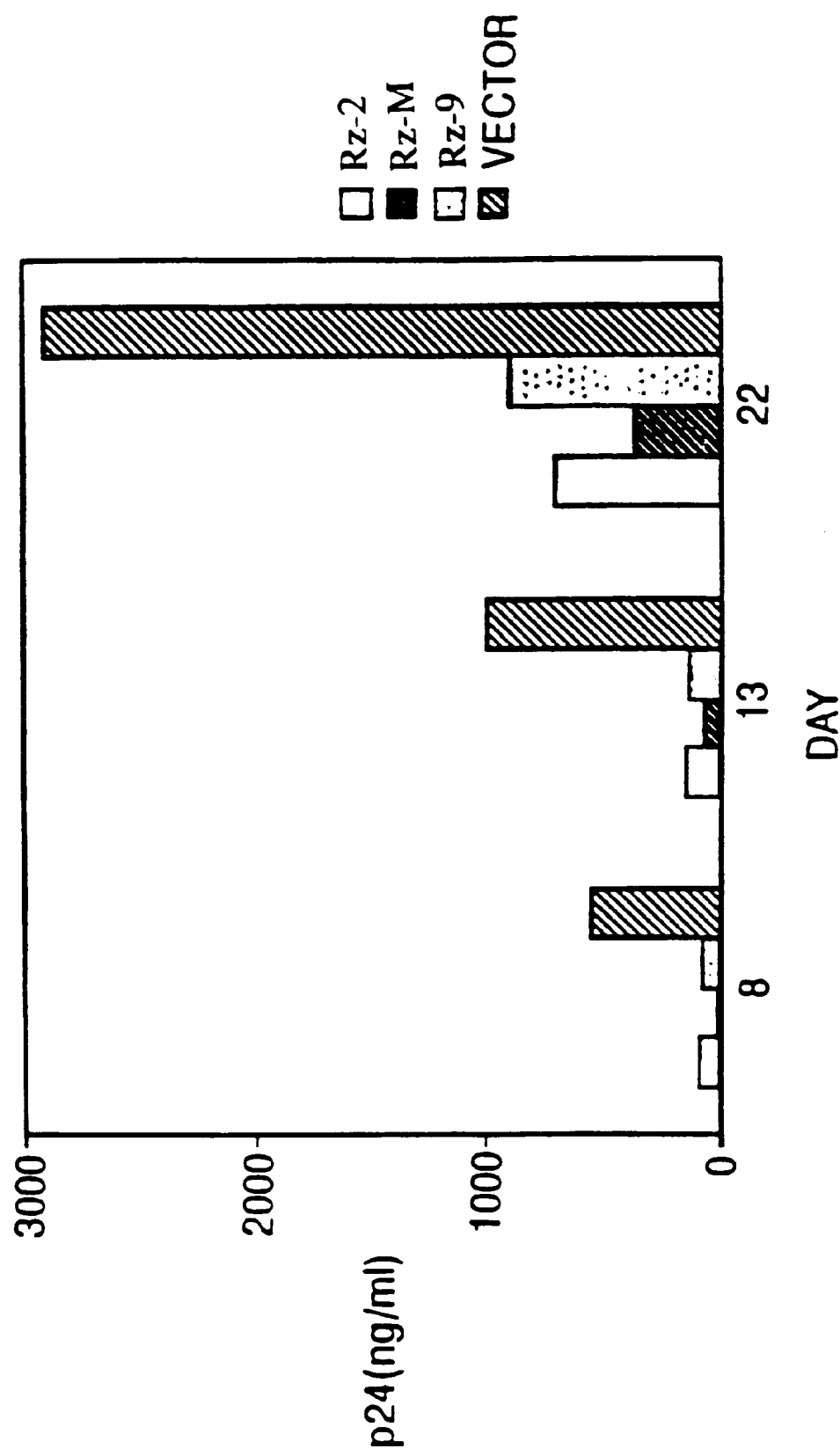
FIG. 10. p24 levels in long term assay The histogram chart shows data for HIV replication as measured by p24 levels at days 8, 13 and 22 for ribozyme 9(Rz-9), the ribozyme construct targeted to the HIV packaging site. Vector, is the control construct. Rz-2 and Rz-M are two ribozyme constructs targeted to the tat gene of HIV. Rz-M is a multi-ribozyme containing several ribozymes targeted to different sites within tat. This includes the site targeted by Rz-2.
Figure 11:
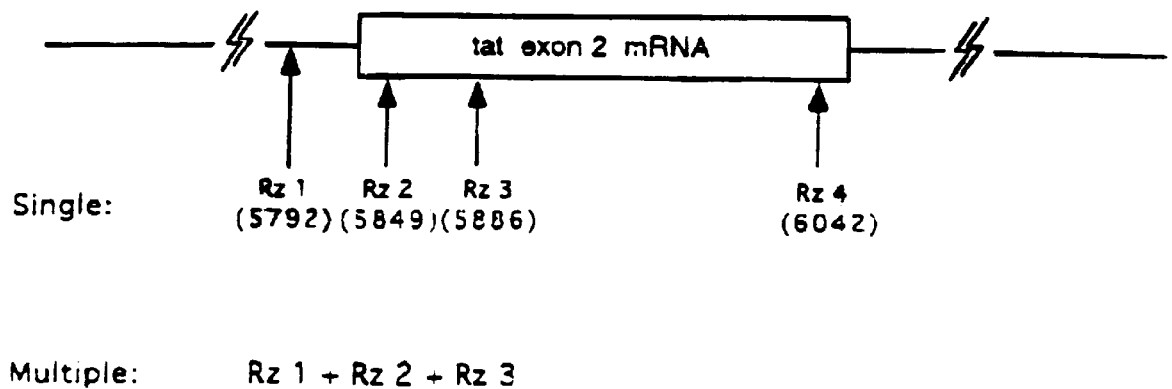
FIG. 11. The anti-HIV-1 tat ribozymes were designed according to the sequence data of HIV-1 SF2 isolate from Genebank (LOCUS: HIVSF2CG) Target sites are GUC (Rz 1), GUA (Rz 2), GUC (Rz 3) and CUC (Rz 4).
Figure 14:
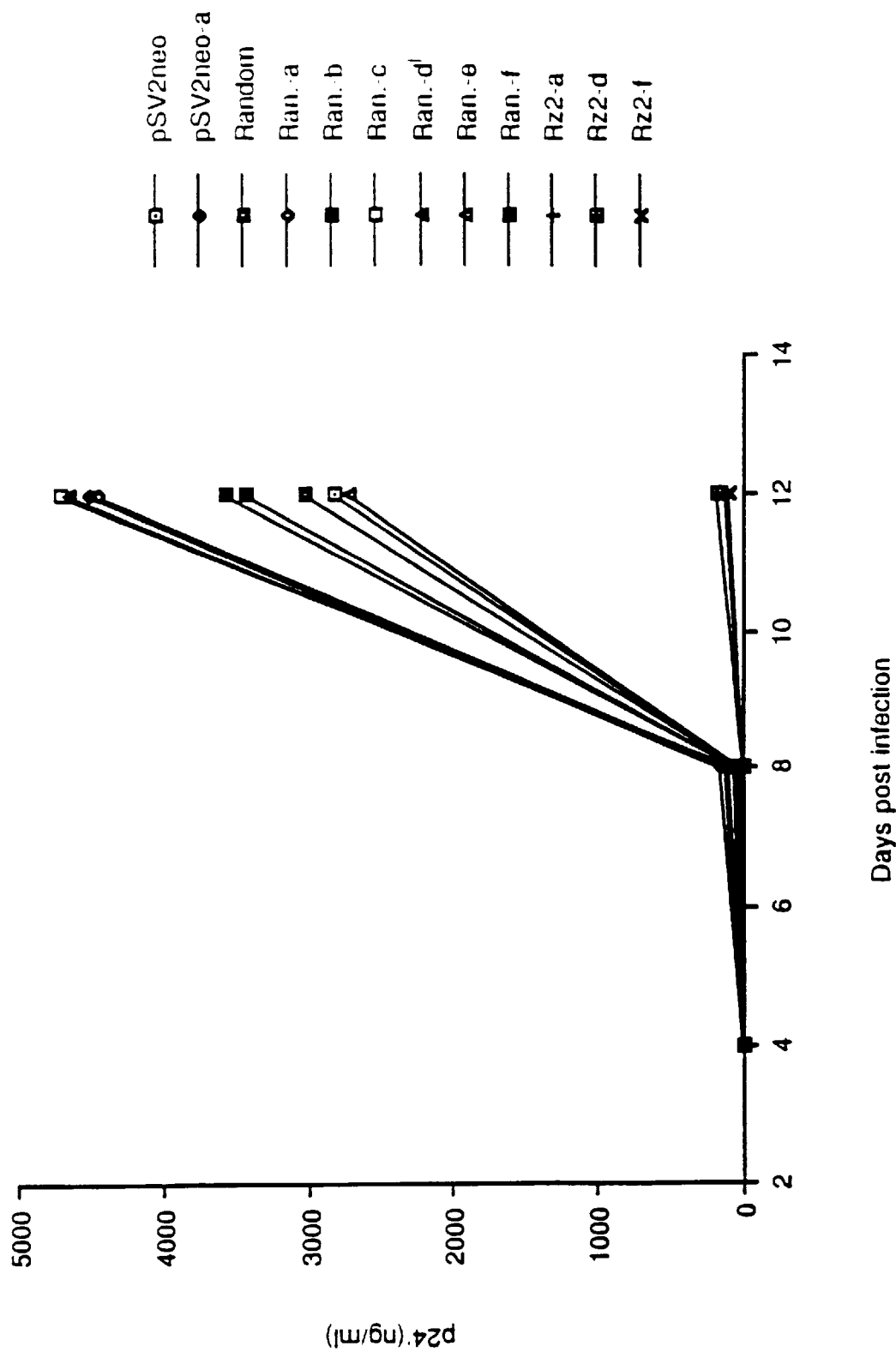
FIG. 14. Transfected clonal T cell lines (Sup T1) showing protection in Rz2 (a,d,f). Clonal cell lines containing vector (pSV2 neo, neo-a) and random controls (Ran a,b,c,d,e,f)

In another experimental protocol, the cells were pelleted, and an aliquot of the supernatant taken for p24 assay. Representative results are shown in FIG. 10. In this experiment there was an inhibition of p24 levels to day 22 post challenge. At days 8 and 13 post-infection, more than an 80% inhibition of p24 production was observed in ribozyme-expressing cells compared to cells containing vector alone, whereas at day 22 an approximately 60% level of inhibition was observed.

These results provide evidence that HIV replication can be inhibited by the addition of a ribozyme against the Psi packaging site into T lymphocytes.

TABLE 3

| | Syncitia Formation | | | |
|---|---|---|---|---|
| Clones | $10^{-3}$ | Virus $10^{-4}$ | Dilution* $10^{-5}$ | $10^{-6}$ |
| Rz-2 | ++++ | +--- | ---- | ---- |
| Rz-M | ++++ | ---- | ---- | ---- |
| Rz-Psi | ++++ | ++-- | +--- | ---- |
| Random | ++++ | ++++ | ++-- | +--- |
| pSV2neo | ++++ | ++++ | ++++ | ++-- |

* HIV-1 (SF33) was used in the infectivity assay (m.o.i. of 0.1–1).

TABLE 4

Syncitia formation of infected SupT1 cells

| | Days Post Infection | | | | | |
|---|---|---|---|---|---|---|
| Group | 6 | 7 | 8 | 9 | 10 | 11 |
| pSV-Rz-HIV Psi | − | − | − | − | − | + |
| pSV2neo | − | + | ++ | +++ | +++ | +++ |
| Mock | − | − | − | − | − | − |

The number of syncitia in each culture was counted in four low-power fields and was averaged, −, no syncytia; +, 1–5 syncytia; ++, 6–10 syncytia; +++, greater than 10 syncytia. Mock is uninfected SupT1 cells.

EXAMPLE 8

We also assessed efficacy of the other (in addition to ψ targeted) ribozyme constructs. Unexpectedly, we found that a single ribozyme targeted to a sequence within the tat gene of HIV-1 (Rz2) was also effective in inhibiting HIV-1 replication. We examined the sequence conservation of this region of tat and found it to be highly conserved amongst different HIV-1 isolates (see FIG. 12). These are the first experiments with this tat sequence as a HIV-1 ribozyme target site. The reports in the literature are noted in FIG. 13 in which the tat target sites noted were targeted by other investigators site 1 (Crisell et al., 1993) and site 3 (Lo et al., 1992 and Zhou et al., 1992).

SUMMARY

Human peripheral blood lymphocytes (PBLs) were transduced with a number of recombinant retroviruses including RRz2, an LNL6-based virus with a ribozyme targeted to the HIV tat gene transcript inserted within the 3' region of the neomycin resistance gene (neo$^r$); RASH-5, an LNHL-based virus containing an antisense sequence to the 5' leader region of HIV-1 downstream of the human cytomegalovirus (HCMV) promoter; and R20TAR, an LXSN-based virus with 20 tandem copies of HIV-1 TAR sequence driven by the Moloney murein leukemia virus long terminal repeat (LTR). After G418 selection, the transduced PBLs were challenged with the HIV-1 laboratory strain IIIB and a primary clinical isolate. Results showed that PBLs from different donors could be transduced and that this conferred resistance to HIV-1 infection. For each of the constructs, a reduction of approximately 70% in p24-antigen level relative to the corresponding control vector transduced PBLs was observed. Molecular analyses showed constitutive expression of all the transduced genes from the retroviral LTR— but no detectable transcript was seen from the internal HCMV promoter for the antisense construct. Transduction of, and consequent transgene expression in, PBLs did not impact on the surface expression of either $CD4^+/CD8^+$ (measured by flow cytometry) or on cell proliferation (examined by [$^3$H]thymidine uptake assay). These results indicate the potential utility of these anti-HIV-1 gene therapeutic agents and show the pre-clinical value of this PBL assay system.

The human immunodeficiency virus (HIV) has been identified as the etiological agent of Acquired Immunodeficiency Syndrome (AIDS) and its associated disorders (Barre-Sinoussi, F. et al. 1983; Gallo, R. C. et al. 1984). At present, there is no adequate treatment for this disease and the use of genetic manipulation to inhibit HIV replication appears to be a novel and promising approach to AIDS therapy. Possible gene therapeutic approaches to intervene in aspects of HIV-1 replication include the use of ribozyme expression to catalytically cleave and thus inactivate HIV-1 RNA; antisense RNA expression to inhibit reverse transcription, processing and translation of HIV RNA; expression of mutant HIV structural or regulatory genes with dominant repression activity; and expression of RNA decoys to inhibit HIV-1 transcription, processing and packaging.

In published reports to date, retroviral vectors have been the chosen delivery method for the introduction of transgenes and gene therapeutic anti-HIV-1 agents. These vectors have been tested in human hematopoietic T lymphocytic cell lines, such as CEM, SupT1 and MOLT-4 (Sarver, N. et al. 1990; Weerashingee, M. et al. 1991; Yu, M. et al. 1993; Yamada, O. et al. 1994; Rhodes, A. and James W. 1991; Sczakiel, G. et al. 1992; Lisziewicz, J. et al. 1991, 1993; Trono, D. et al. 1989; Malim, M. H. et al. 1992) that have several desirable characteristics, including unlimited growth potential for in vitro assays, but the disadvantage of being transformed cells. Therefore, it is necessary to test efficacy of anti-HIV gene therapeutic agents in human primary cells, such as peripheral blood lymphocytes (PBLs). For these cells, it is the $CD4^+$ sub-population which is the key target cell for HIV infection and it is this cell population that is primarily depleted in AIDS patients. However, at present there are no reports in which primary PBL assays have been used for anti-HIV gene therapeutic approaches.

We have conducted a comprehensive study on human PBLs to i) test anti-HIV agents, including ribozyme, antisense and RNA TAR decoys, and ii) establish the conditions for PBL transduction, G418 selection and HIV-1 challenge using both laboratory and clinical HIV-1 isolates. This experiments demonstrate that transduction of primary PBLs with retroviral constructs expressing a ribozyme targeted to the HIV-1 tat gene; an antisense sequence complementary to the 5' leader region of HIV-1; or a 20 TAR RNA decoy, conferred substantial resistance to HIV-1 infection. This assay system is an improvement upon previous assays of anti-HIV retroviral constructs and serves to complement present T cell line assays. By using this system, we have generated significant data of clinical relevance to HIV gene therapy.

MATERIALS AND METHODS

Cell Lines: Packaging cell lines Ψ2 (Mann, R. et al. 1983) and PA317 (ATCC CRL 9078) were cultured in Dulbecco's modified Eagle's medium (DME) containing 10% fetal bovine serum (FBS). PA317 cells were subjected to selection (5 to 7 days) every six weeks in HAT medium. ΨCRE and ΨCRIP (Danos, O. and Mulligan, R. C. 1988) were grown in DME plus 10% bovine calf serum (BCS).

Figure 15A:
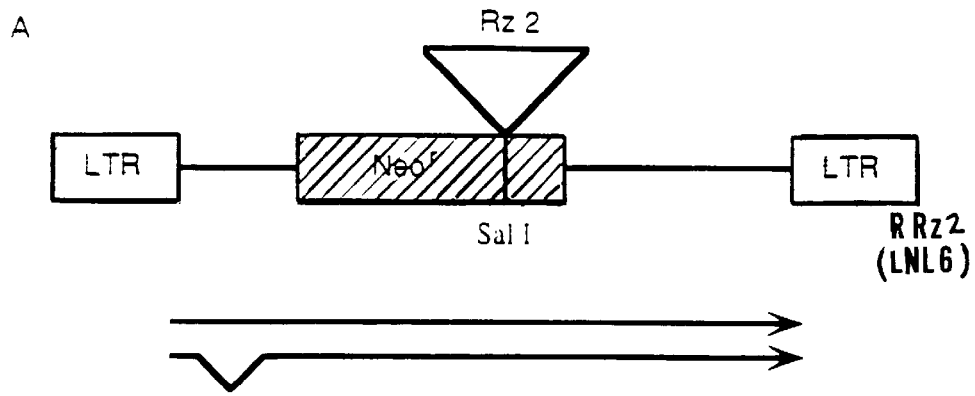
FIG. 15A–15C Schematic representation of the retroviral vector constructs and their consequent expression (not drawn to scale). 15A, ribozyme construct RRz2; 15B, antisense construct RASH5; 15C, polymeric-TAR construct R20TAR. The parental retroviral vectors are denoted in parentheses. See text for details.
Figure 15B:
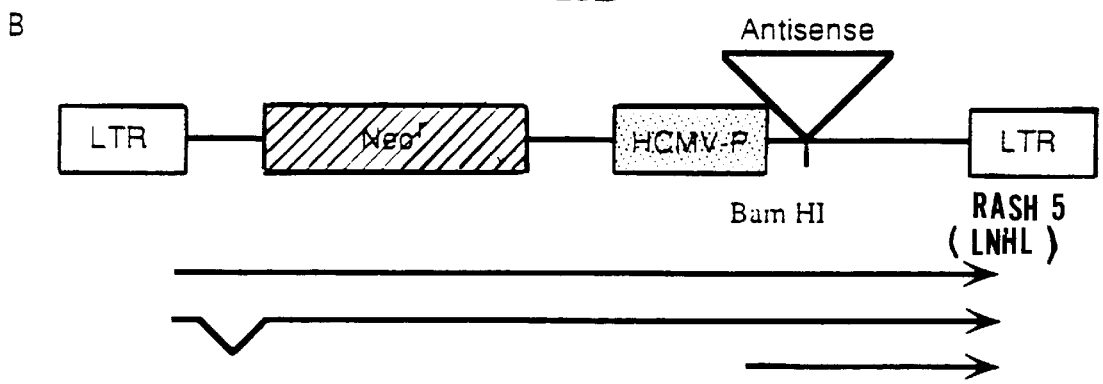
Figure 15C:
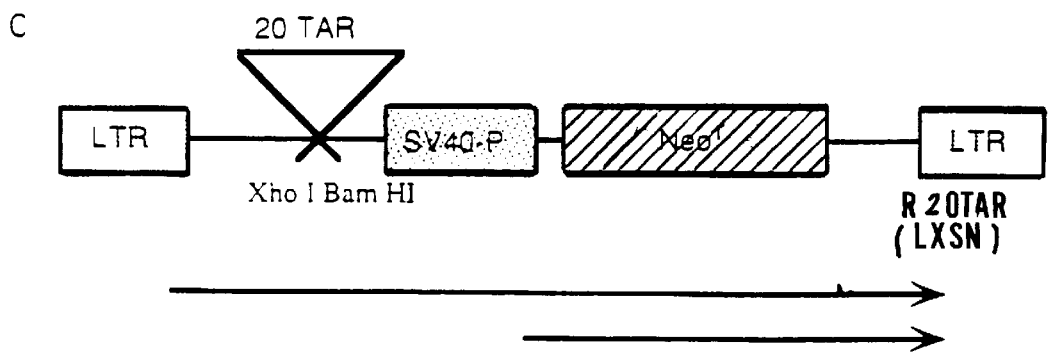

Retroviral Vector Constructions: A chemically synthesized hammerhead ribozyme targeted to the HIV-1 tat gene transcript (nt 5865 to nt 5882 of HIV-1 IIIB, GGAGCCA GTAGATCCTA, SEQ ID NO:8) was cloned into a SalI site of the LNL6 vector (Bender, M. A. et al. 1987) within the 3' untranslated region of the neomycin resistance gene (FIG. 15A). This construct was named RRz2. For the antisense construct, a 550 bp BamHI fragment of the HXB2 clone containing part of R, U5 and 5' portion of the gag gene (nt 78 to nt 628) was cloned in an antisense orientation into a BamHI site of the LNHL vector (FIG. 15B) which was derived from the pNHP-1 vector by removing the human HPRT cDNA at BamHI site (Yee, J. K. et al. 1987). The resultant antisense construct was called RASH5. The polymeric-TAR construct was made by inserting a 20TAR fragment (20 tandem copies) into XhoI and BamHI sites within the LXSN vector (Miller, A. D. et al. 1989) and termed R20TAR (FIG. 15C). The sequence integrity and orientation of the constructs were confirmed by either DNA sequencing or restriction enzyme mapping.

Production of Amphotropic Retroviruses: The retroviruses LNL6 and RRz2 were produced by trans-infection involving the packaging cell lines Ψ2 and PA317 cells. Approximately 80% confluent Ψ2 cells were transfected with 10 μg of the construct DNA by using calcium precipitation and incubating in DME medium containing 10% FBS (DME growth medium) for 14 hr. This medium was then removed, replaced with fresh DME growth medium and incubated overnight at 37° C., 5% $CO_2$. Ecotropic viral supernatant was then collected from the transfected Ψ2 cells and used to infect sub-confluent (60–80%) PA317 cells in DME growth medium in the presence of 4 μg/ml polybrene. After 24 hr incubation at 37° C., 5% $CO_2$, the infected PA317 cells were trypsinised and split 1:20 into DME growth medium containing 750 μg/ml G418. The medium was changed every 3 to 4 days until colonies formed. 10 to 29 clones from each of the constructs were picked and expanded for viral titre (neomycin resistant colony assay) and replication-competent retrovirus (RCR) assays (Miller, A. D. and Rosma, G. J. 1989). The retroviruses LNHL, RASH5, LXSN and R20TAR were produced by transfecting ΨCRE and infecting ΨCRIP cells. 20 to 96 clones of each construct were isolated for titre and RCR assays.

Transduction of Human PBLs: Peripheral blood mononuclear cells (PBMCs) were prepared from leukopacks of healthy donors by Ficoll-Hypaque gradient centrifugation. CD4$^+$ cells were enriched by depletion of CD8$^+$ cells using a MicroCELLector Flask (Applied Immune Science) according to the manufacturer's instructions. The CD4$^+$ enriched PBLs (5×10$^5$ cells/ml) were stimulated using 5 μg/ml of phytohemagglutinin (PHA, Sigma) or 10 ng/ml of the OKT3 monoclonal antibody (Janssen-Cilag) in RPMI-1640 medium supplemented with 10% FBS and 20 units/ml of human recombinant interleukin 2 (RPMI growth medium) for 48 to 72 hr. The stimulated PBLs were transduced by exposure of the cells to a producer cell-free retroviral stock for 18 hr in the presence of 4 μg/ml polybrene (an m.o.i. of 0.5 was employed). Forty eight hours after transduction, PBLs were selected in RPMI growth medium containing 300 to 500 μg/ml of G418 for 10 to 14 days. This was followed by a recovery period of one week in fresh RPMI growth medium without G418 before the PBLs were challenged with HIV-1.

HIV-1 Infection: The infectious titers (TCID50) of HIV-1 laboratory strain IIIB and clinical isolate 82H were determined on human PBLs as described (Johnson, V. A. et al. 1990). 5/10$^5$ transduced PBLs were infected with 100 TCID50 HIV virus for 2 hr at 37° C. followed by washing cells twice with RPMI-1640 and resuspending cells in 5 ml of RPMI growth medium. Every 3 to 4 days, aliquots of the supernatant were sampled for p24 antigen ELISA (Coulter).

RNA Analysis: Total cellular RNA was extracted using guanidium-isothiocyanate method (Chirgwin, J. J. et al. 1979) from transduced PBLs. 15 μg RNA was fractionated on a 1% agarose-formaldehyde gel, transferred to a nylon membrane (Hybond-N) and hybridized with $^{32}$P-labelled neo$^r$-specific probe, 550 bp BamHI fragment of HIV-1 HXB2 or 20 TAR fragment for detection of neo$^r$-ribozyme, antisense and TAR expression respectively.

FACS Analysis of Transduced PBLs: 1×10$^5$ transduced PBLs were incubated for 20 min at 4° C. with CD4 or CD8 specific fluorescein isothiocyanate (FITC) -conjugated monoclonal antibodies (Becton Dickinson) or with a control antibody (FITC-mouse IgG1, Becton Dickinson). After two washes in PBS, the cells were analyzed on a Becton Dickinson FACScan.

Proliferation Assay: PBLs were transduced as described above. Following selection in G418 and recovery in fresh RPMI growth medium, viability was assessed by trypan blue exclusion, and cell numbers were adjusted to 1×10$^6$ viable cells/ml. Triplicate wells (Corning 24 well-plates) were seeded with 1×10$^6$ cells and 1 μCi 6-[$^3$H]-thymidine (5 Ci/mmol, Amersham) was added to each well. After 48 hr in culture, cells were transferred to glass fibre filters under vacuum, washed three times with ice-cold phosphate buffered saline, and precipitated with 3×5 ml ice-cold 10% trichloroacetic acid (w/v). Filters were rinsed with ethanol and subjected to β-scintillation counting. Statistical analysis was performed using Student's t-test.

RESULTS

Generation of High-Titre Amphotropic Retroviruses Containing Various Transgenes. Three different retroviruses expressing the transgenes (ribozyme, antisense or polymeric-TAR) were constructed based on the different vector backbones. RRz2 was constructed by inserting an anti-HIV tat ribozyme gene into the 3' untranslated region of neo$^\gamma$ gene driven by the MoMLV long terminal repeat (LTR) in the LNL6 vector (FIG. 15A). A chimeric RNA transcript containing both the neo$^\gamma$ and ribozyme genes is expected from this retrovirus. In the RASH5 retrovirus (FIG. 15B), the antisense sequence could be transcribed from either the viral LTR or the internal human CMV promoter. In the R20TAR construct, polymeric-TAR is expressed from the viral LTR (FIG. 15C). The three retroviral constructs and the corresponding control vectors were used to generate amphotropic producer cell lines. Viral titres were within the range 10$^5$ to 5×10$^6$ cfu/ml, as measured by a standard protocol (Miller, A. D. and Rosma, G. J. et al. 1989). In general, retroviral titres of >10$^6$ cfu/ml were used in transduction experiments. All the viral stocks were tested and confirmed to be free of RCR, and stored at −80° C.

Retroviral Transduction of PBLs. To optimize the stimulation of PBLs for retroviral transduction, the responses of CD4$^+$ enriched PBLs to PHA or the OKT3 antibody were compared. No difference was observed within the cultures using either PHA or OKT3 in terms of cell doubling time, viability and the transduction capacity. In the present experiments, the OKT3 antibody was used because it has been approved for use in humans. The stimulated PBLs were then transduced with the amphotropic retroviruses using an m.o.i. of 0.5. Determination of the relative transduction efficiency was based on the number of cells which survived G418 selection. The overall transduction efficiency was found to vary from 2–7% depending on the donor blood packs.

G418 selection of the transduced PBLs was shown to be a crucial step within the PBL assays. To achieve complete selection, a two-step procedure was employed. For each batch of PBLs, a G418 toxic dose assay was set up and simultaneously, a base-line G418 concentration of 300 μg/ml was applied to the transduced PBLs in the initial 7 to 9 days. After this initial period, the G418 concentration was adjusted to that determined within the toxic dose assay. For the 10 donors tested, it was found that the G418 toxic dose ranged from 300 to 500 μg/ml using an initial cell concentration of 10$^5$ cells/ml. After transduction and selection, the PBLs were then cultured in fresh medium without G418 for a week. This recovery step is important in order to enhance cell viability and increase cell numbers (a 3 to 5 times increase was found relative to that seen with G418) for the subsequent HIV-1 challenge assays.

Figure 16A:
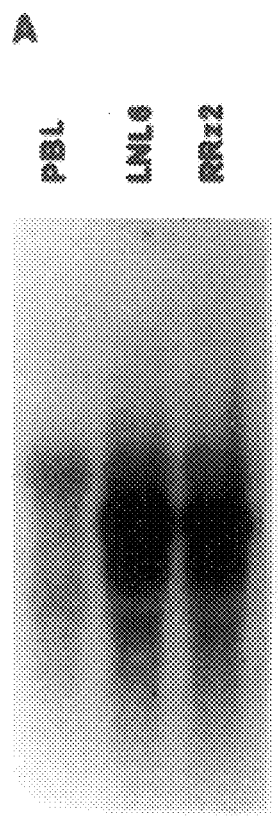
FIG. 16A–16C Expression of the retroviral constructs in the transduced PBLs. The expression of ribozyme (FIG. 16A), antisense (FIG. 16B) and 20TAR RNA (FIG. 16C) was examined by Northern analysis using the corresponding $^{32}$p-labelled probes. See text for details.
Figure 16B:
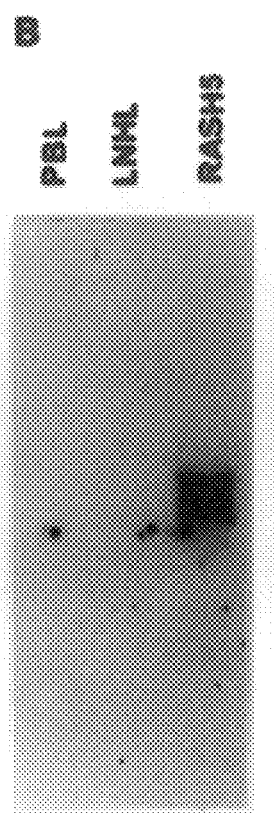
Figure 16C:
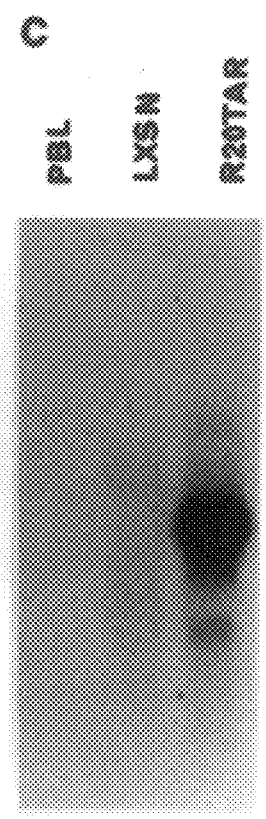

Expression of the Transgenes in the Transduced PBLs. The expression of ribozyme, antisense or TAR sequence in the transduced PBLs was evaluated. FIG. 16A–16C shows the representative pattern of Northern analysis. In RRz2 and LNL6 transduced cells (FIG. 16A), both spliced and unspliced transcripts containing neo$^r$-ribozyme or neo$^r$ messages were detected using a neo$^r$ specific probe (3.2 kb and 2.4 kb). The predominant RNA species was the unspliced transcript. When the blot was hybridized with a ribozyme specific probe, the same pattern was observed for RRz2 RNA only. In RASH5 transduced PBLs, two transcripts from the 5' LTR (spliced and unspliced) were detected using the 550 bp probe and confirmed to be expected sizes (4.8 kb and 4.0 kb) (FIG. 16B). However, the shorter transcript expected from the internal CMV promoter was not expressed, indicating that the CMV promoter had been shut off in this construct. The R20TAR vector generated an unspliced 4.6 kb transcript from the 5' LTR hybridizing to the TAR probe as expected (FIG. 16C) due to inactivation of the splice donor in LXSN.

Figure 17A:
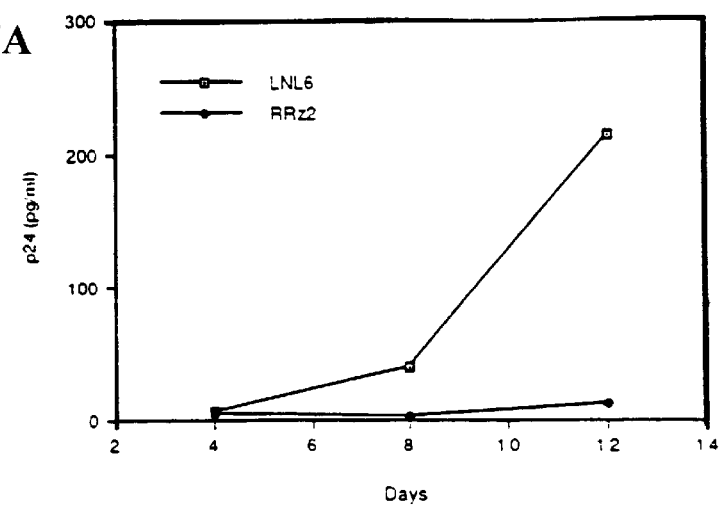
FIG. 17A–17C Inhibition of HIV-1 IIIB replication in transduced PBLs. The transduced and selected PBLs were challenged and assayed as described in Material and Methods. The data plotted are the means from five donors (FIG. 17A, ribozyme constructs and FIG. 17B, antisense constructs) and two donors (FIG. 17C, polymeric-TAR constructs).
Figure 17B:
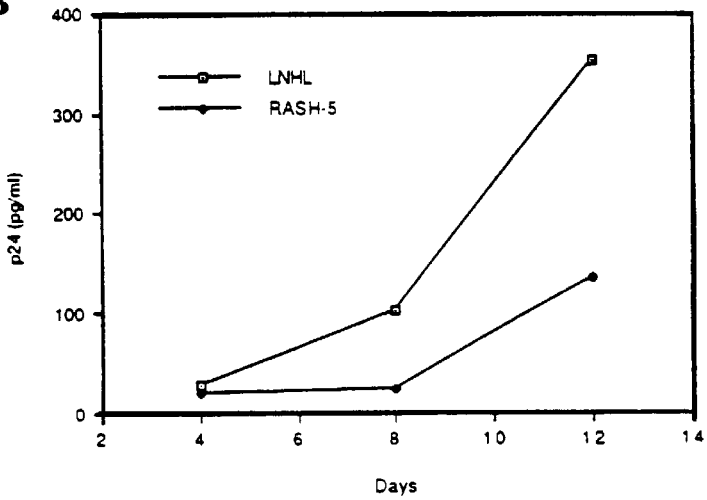
Figure 17C:
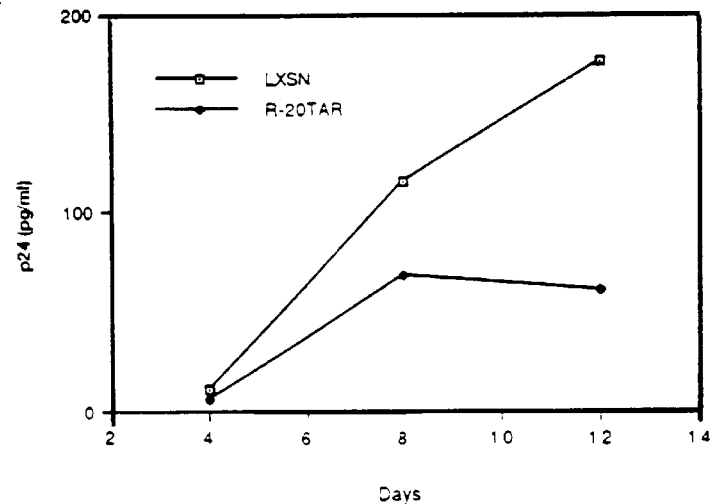
Figure 18A:
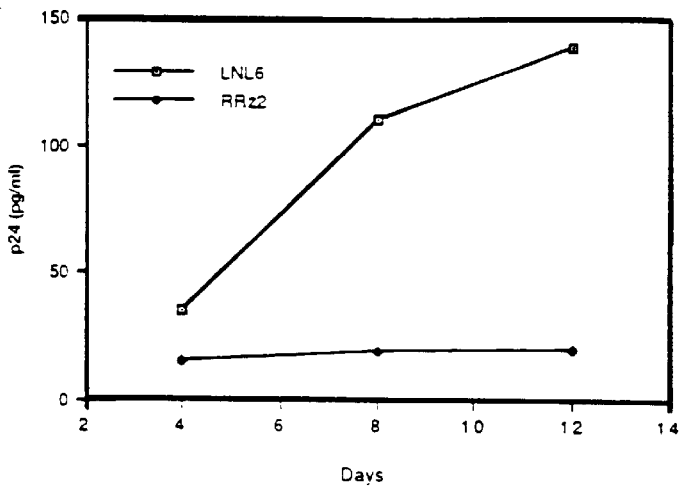
FIG. 18A–18C Resistance of transduced PBLs to infection by a clinical isolate 82H. The PBLs were transduced with the ribozyme construct (FIG. 18A), antisense construct (FIG. 18B) and polymeric-TAR construct (FIG. 18C), infected with 82 H as described in Materials and Methods. The data plotted are the means from two donors.
Figure 18B:
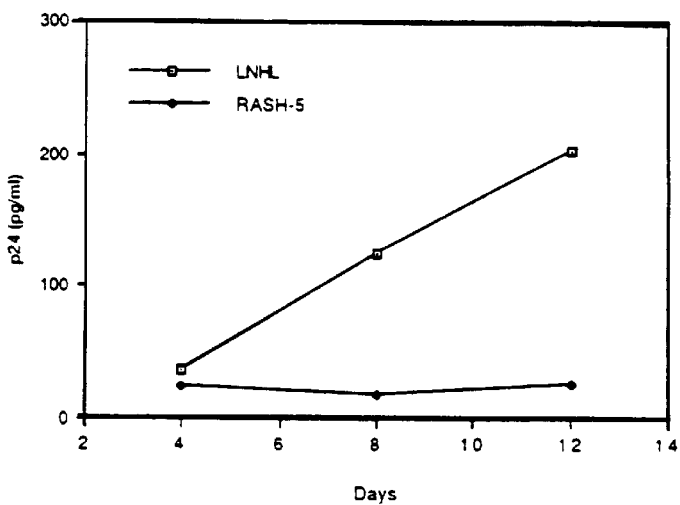
Figure 18C:
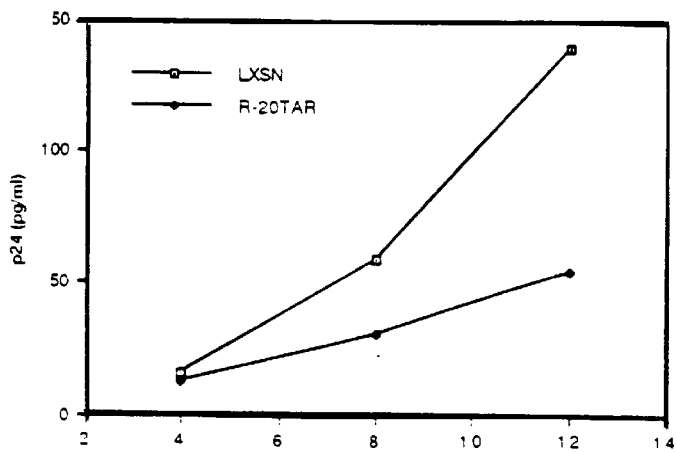

Inhibition of HIV-1 Replication in Human PBLs. To analyze the relevance of the PBL assay system to the study of HIV-1 gene therapy, HIV challenge experiments were conducted on transduced PBLs using both the laboratory strain (IIIB) and a primary clinical isolate (82H). The infections were done in duplicate and repeated with three to five independent batches of PBLs. HIV-1 replication was monitored at various time points by measuring p24 antigen levels in the culture supernatant. In the challenge experiments using HIV-1 IIIB strain, p24 production was markedly reduced (70%) in the PBLs expressing ribozyme (FIG. 17A), antisense (FIG. 17B) and TAR decoy (FIG. 17C) in relation to PBLs transduced with corresponding control vectors. Inhibition to a lesser degree (40% compared to 70%) was also observed in the transduced, but not selected PBLs. Transduced and selected PBLs were also assessed for their resistance to the infection of a primary HIV-1 isolate. The primary clinical isolate 82H was directly obtained from patient's PBMCs, and has been characterized as a T-cell tropic and syncytia-inducing isolate. As for IIIB, 82H replication (assayed by p24 antigen ELISA) was inhibited to a similar level seen in HIV-1 IIIB infected PBLs (FIG. 18A–18C). These results indicate that these transgenes delivered into human PBLs through retroviral vectors can inhibit HIV-1 replication in primary hematopoietic cells.

Figure 19:
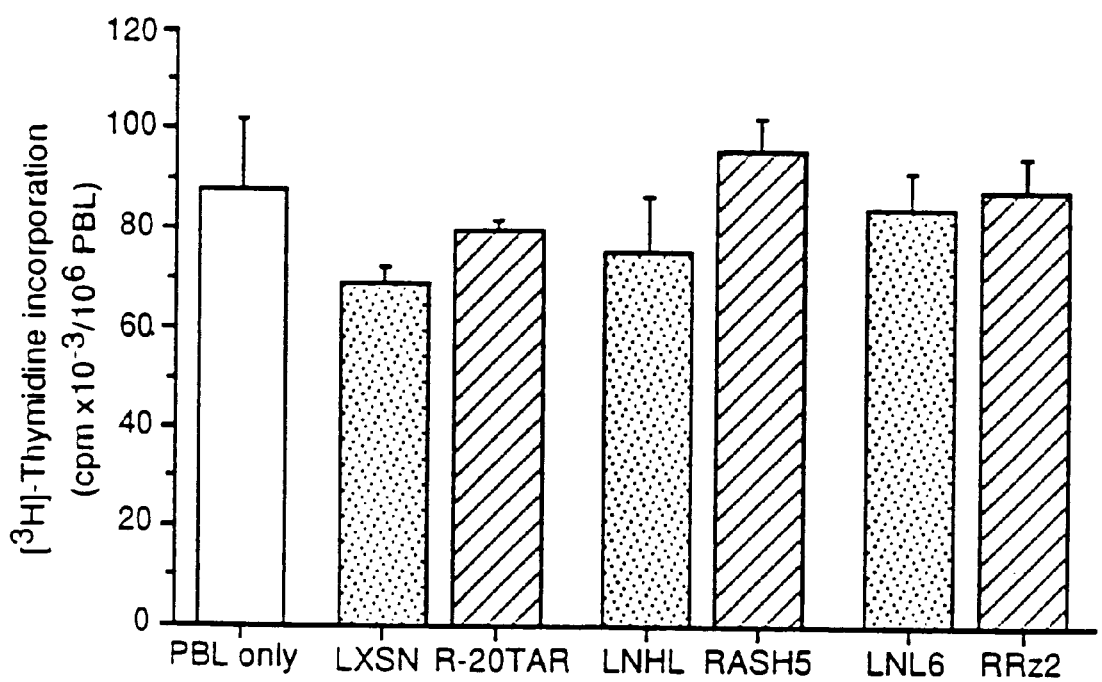
FIG. 19 Proliferation assays of the transduced PBLs. The data are shown as mean±SD (n=3). PBL only, untransduced PBLs; LXSN, R-20TAR, LNHL, RASH-5, LNL6 and RRz2, transduced PBLs with the corresponding retroviruses.
Figure 20:
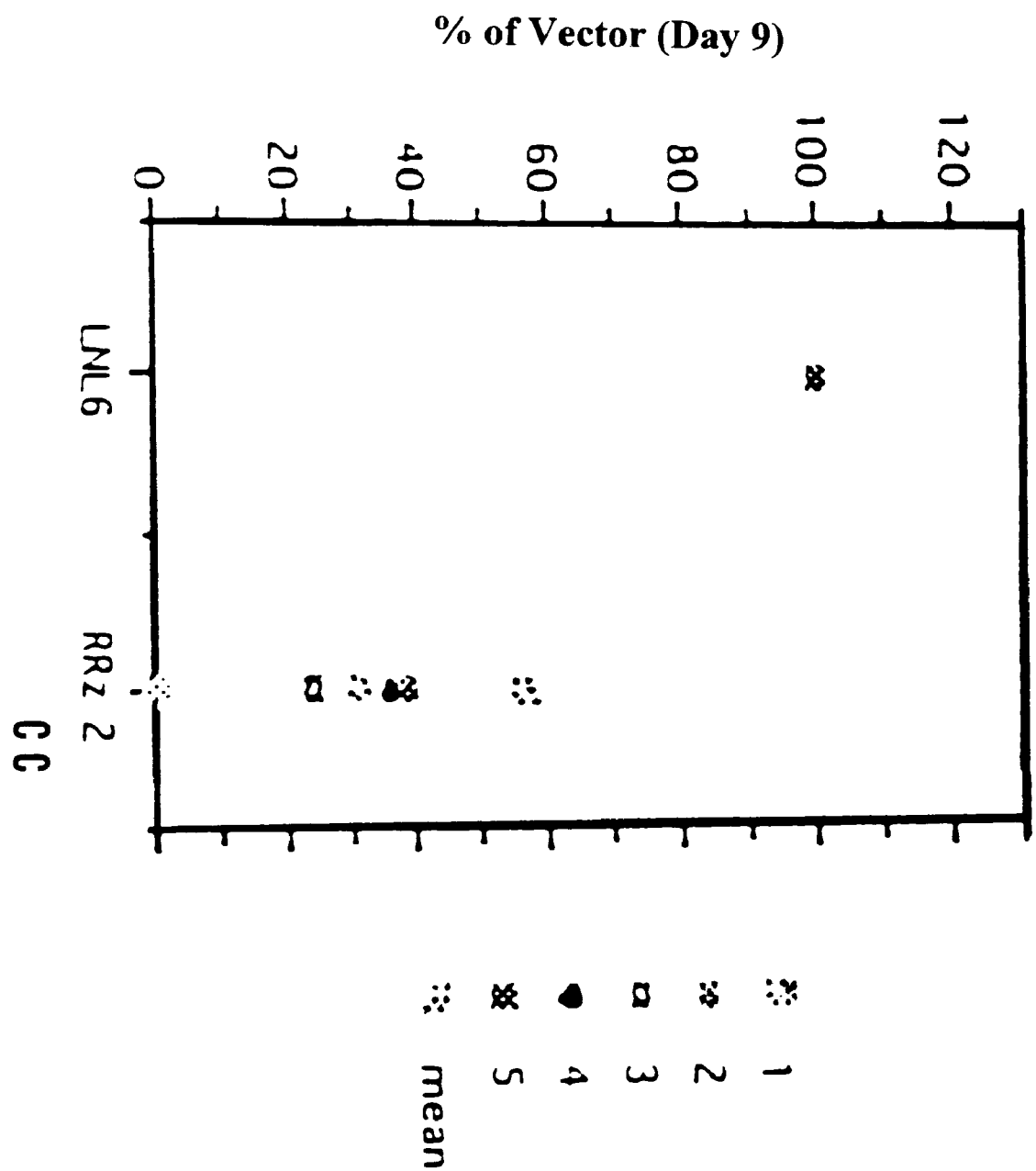
FIG. 20 CEM T4 T-lymphocyte cell line is transduced with virus and subjected to G418 selection. The pooled population contains cells with random integrants and variable construct expression levels which are then challenged with HIV-1.
Figure 21A:
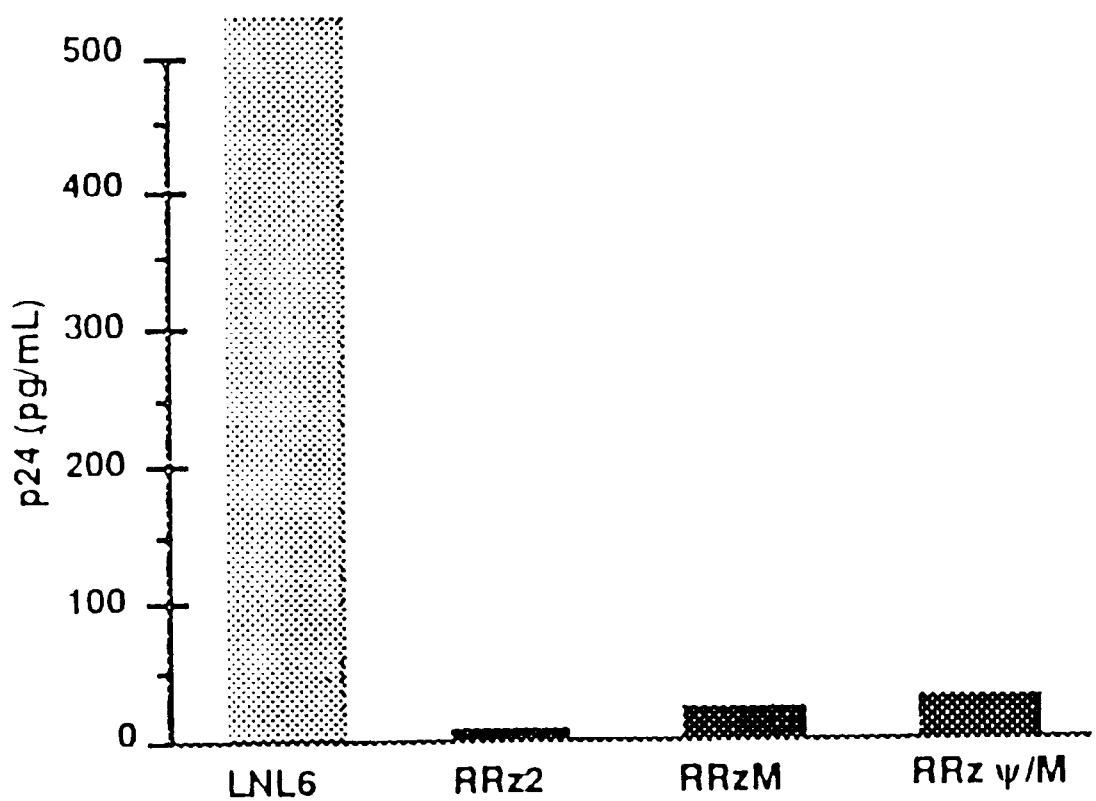
FIG. 21A–21B RzM is multiple ribozyme directed against TAT and RRzpsi/M is ribozyme directed against the packaging/multiple ribozyme against tat together.
Figure 21B:
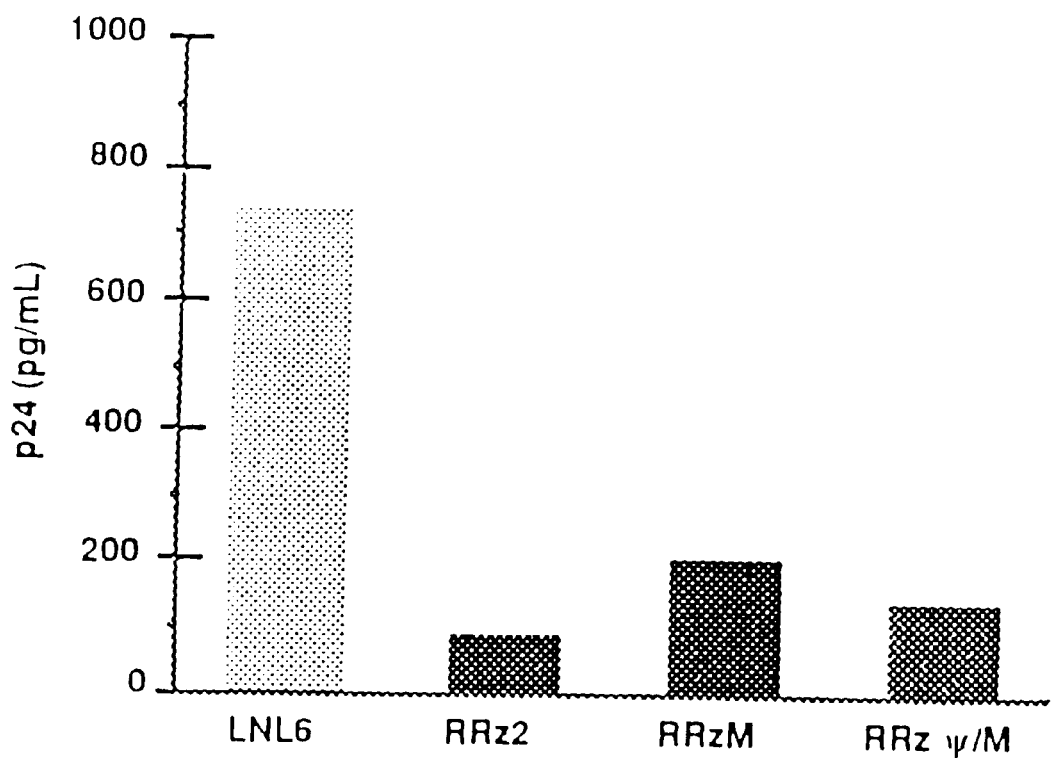

Analysis of Transduced PBLs. To investigate potential effects of transduction and construct expression on PBL proliferation, [$^3$H]-thymidine-uptake assays were performed on all the transformed and selected PBLs. When compared with non-transduced normal PBLs, there were no obvious deleterious effects in transgene construct and vector transduced PBLs (P <0.02); (FIG. 19). In addition, FACS analysis revealed that CD4 surface marker remained unchanged after transduction (Table 5). This demonstrated that the inhibitory effect observed in HIV-1 challenge assays was not due to a reduction in the number of CD4 receptors on the transduced PBLs.

TABLE 5

CD4/CD8 Surface Markers on PBLs as Measured by FACS Analysis

| Cells* | Percentage Cells (%) | |
|---|---|---|
| | CD4$^+$ | CD8$^+$ |
| Total PBLs | 83.80 | 8.40 |
| CD4$^+$PBLs | 93.65 | 0.42 |
| LNL6-PBLS | 93.01 | 1.19 |
| RRz2-PBLS | 94.02 | 0.92 |

*PBLS were analyzed as described in Materials and Methods. Total PBLs = untransduced total PBLs; CD4$^+$ PBLs = untransduced CD4$^+$ enriched PBLs; LNL6-PBLs = CD4$^+$ enriched PBLs transduced with LNL6 virus; RRz2-PBLs = CD4$^+$ enriched PBLs transduced with RRz2 virus.

DISCUSSION

In order for gene therapy to be ultimately used to inhibit HIV-1 replication in vivo, such gene therapeutic approaches must first be examined in experimental systems. To date, these experimental systems have mainly involved the use of human T lymphocytic cell lines, and no published data is available in primary PBLs (Yu, M. et al. 1994). In order to generate pre-clinical data, it is important to test anti-HIV-1 gene therapeutic agents in primary hematopoietic cells. These cells are the major targets for HIV-1 infection and replication and there are significant differences in growth characteristics, response to in vitro manipulation and reactivity to HIV-1 infection between cell lines and PBLs. It is the CD4$^+$ PBL population of HIV-1 gene therapy. For these reasons, we have conducted the present study to establish a PBL assay system.

In this study, three different retroviral vectors expressing ribozyme, antisense or TAR decoy genes have been tested for their anti-viral efficacy in human PBLs. Although they were constructed in different retroviral vectors, they were all shown to be effective at a similar level in HIV-1 protection assays with no apparent cytotoxicity, as measured by $^3$H-thymidine incorporation assay and FACS analysis. These observations show the feasibility of PBLs as target for HIV-1 gene therapy.

To utilize PBLs as either an assay system or as therapeutic target cells, several points should be noted. Firstly, high viral titre is a crucial factor to achieve efficient transduction of PBLs. This is especially the case for clinical purposes where it may not be desirable to select transduced PBLs with G418. We tested both selected and unselected PBLs which were transduced with high titre therapeutic retroviruses (>10$^6$ cfu/ml). It was found that the unselected PBLs were also resistant to HIV-1 infection although the degree of inhibition was lower than that found in the selected PBLs, suggesting that it is clinically possible to use ex vivo transduced PBLs without G418 selection. G418 selection, however, may enable low titre virus to be used for in vitro testing of gene therapeutics. We have developed a two-step G418 selection procedure by which complete selection can be readily achieved. These procedures minimize the time of in vitro culture thereby serving to reduce any modification to the T cell population. In our experiments, continuous culture of PBLs in vitro for two weeks did not significantly impact on the surface markers (CD4$^+$ and CD8$^+$). This length of period (two weeks) may be sufficient for any ex vivo manipulation of PBLs for therapeutic purposes.

Retroviral vector design is another important aspect for efficient gene transfer and expression. Although no direct comparison can be made among the three vector designs used in this study, two observations are of note. First, all the transgenes controlled by the viral LTR (but not from the CMV internal promoter for one construct) were efficiently expressed in a constitutive manner in human primary hematopoietic cells. Secondly, the strategy whereby a ribozyme gene is inserted into the 3' untranslated region of a gene such as neo$^r$ in the retroviral vector appears to be as efficient in PBLs as it is in T cell lines. These observations may be useful for future improvements in gene therapeutic design.

In conclusion, transduction of human primary PBLs and their protection from HIV-1 infection ex vivo can be accomplished using the protocols presented in this disclosure. This will not only provide a useful system for assessment of gene therapeutic agents in vitro, but also forms the basis for HIV-1 gene therapy targeted to CD4$^+$ lymphocytes.

TABLE 7

Animal Retroviruses

AIDS-related virus (ARV)

Avian Erthyroblastosis Virus

Avian Leukosis Virus (or Lymphoid Leukosis virus)

Avian Myeloblastosis Virus

Avian Reticuloendotheliosis Virus

Avian Sarcoma Virus

Baboon Endogenous Virus

Bovine Leukemia Virus

Bovine Lentivirus

Bovine Syncytial Virus

Caprine Encephalitis-Arthritis Virus (or Goat Leukoencephalitis Virus)

Avian Myelocytomatosis virus

Corn Snake Retrovirus Chicken Syncytial virus
Duck Infectious Anemia Virus
Deer Kidney Virus
Equine Dermal Fibrosarcoma Virus
Equine Infectious Anemia Virus
Esh Sarcoma Virus
Feline Immunodeficiency Virus
Feline Leukemia Virus
Feline Sarcoma Virus
Feline Syncytium-forming virus
Fujinami Sarcoma Virus
Gibbon Ape Leukemia Virus (or Simian Lymphoma Virus or Simian Myelogenous Leukemia Virus)
Golden Pheasant Virus
Human Immunodeficiency Virus 1 (HIV-1)
Human Immunodeficiency Virus 2 (HIV-2)
Human T-Lymphotrophic Virus 1 (HTLV-1)
Human T-Lymphotrophic Virus 2 (HTLV-2)
Human T-Lymphotrophic Virus 3 (HTLV-3)
Lymphoproliferative Disease Virus
Myeloblastosis-associated virus
Myelocytomatosis Virus
Mink Cell Focus-Inducing Virus
Myelocytomatosis Virus 13
Mink Leukemia Virus
Mouse Mammary Tumor Virus
Mason-Pfizer Monkey Virus
Murine Sarcoma Virus
Myeloid Leukemia Virus
Myelocytomatosis Virus
Progressive Pneumonia Virus
Rat Leukemia Virus
Rat Sarcoma Virus
Rous-Associated Virus 0
Rous-Associated Virus 60
Rous-Associated Virus 61
Reticuloendotheliosis-Associated Virus
Reticuloendotheliosis Virus
Reticuloendotheliosis Virus-Transforming
Ring-Necked Pheasant Virus
Rous Sarcoma Virus
Simian Foamy Virus
Simian Immunodeficiency Virus
Spleen Focus-Forming Virus
Squirrel Monkey Retrovirus
Spleen Necrosis Virus
Sheep Pulmonary Adenomatosis/Carcinoma Virus
Simian Sarcoma-Associated Virus (or Wooly Monkey Leukemia Virus)
Simian Sarcoma Virus (or Wooly Monkey Virus)

TABLE 9

Table of Packaging Sequences

1. Reticuloendotheliosis virus (Rev) Genome: Wilhelmsen, et al. *J. Virol.* 52:172–182 (1984). bases 1–3149; Shimotohno, et al. *Nature* 285:550–554 (1980). bases 3150–3607. *Packaging Sequence* (ψ):144-base between the Kpn I site at 0.676 kbp and 0.820 kbp relative to the 51 end of the provirus. J. Embretson and H. Temin *J. Virol.* 61(9):2675–2683 (1987).

2. Human immunodeficiency virus type 1 (HIV-1) *Genome:* Gallo et al. *Science* 224:500–503 (1984) *Packaging Sequence* (ψ): 19 base pairs between the 5' LTR and the gag gene initiation codon. A. Lever, *J. Virol.* 63(9) 4085–4087 (1989).

3. Moloney murine leukemia virus (Mo-MuLV) *Genome:* Shinnick, et al. *Nature* 293:543–548 (1981). *Packaging sequence* (ψ):350 nucleotides between the splice site and the AUG site for coding sequence of gag protein. R. Mann, R. Mulligan and D. Baltimore, *Cell* 33:153–159 (1983). *Second packaging sequence* (ψ+) :Only in the 5' half of the U5 region. J. Murphy and S. Goff, *J. Virol.* 63(1):319–327 (1989).

4. Avian sarcoma virus (ASV) *Genome:* Neckameyer and - Wang *J. Virol.* 53:879–884 (1985). *Packaging sequence* (ψ):150 base pairs between 300 and 600 bases from the left (gag-pol) end of the provirus. P. Shank and M. Linial, *J. Virol.* 36(2):450–456 (1980).

5. Rous sarcoma virus (RSV) *Genome:* Schwartz et al. *Cell* 32:853–869 (1983). *Packaging sequence* (ψ):230 base pairs from 120-base (PB site beginning) to 22-base before gag start codon. S. Kawai and T. Koyama (1984), *J. Virol.* 51:147–153.

6. Bovine leukosis virus (BLV) Genome: Couez, et al. *J. Virol.* 49:615–620 (1984), bases 1–341; Rice et al. *Virology* 142:357–377 (1985), bases 1–4680; Sagata et al. *Proc. Natl. Acad. Sci.* 82:677–681 (1985), complete BLV provirus. *Packaging sequence* (ψ):the present inventors predict that it lies between the end of the primer binding site at about base 340 and the initiation codon for gag at about base 41–8.

REFERENCES

1. Abramova, T. V. et al., (1991) Nucleos. Nucleot. 10, 419.
2. Alford, R. L., Honda, S., Lawrence, C. B. and Belmont, J. W. (1991) Virology 183 611–619.
3. Aronoff, R. and Linial, M. (1991) J. Virol. 65, 71–80.
4. Babe, L. M., Pichuantes, S., and Clark, C. S. (1991) Biochemistry 30, 106.
5. Barre-Sinoussi, F., Chermann, J. C., Rey, F., Nugeyer, M. T., Chamaret, S., Dauguet, C., Axler-Blin, C., Vezinet-Brun, F., Rouzioux, C., Rozenbrum, W. & Montagnier, L. (1983) Science 220, 868–871.
6. Bender, M. A., Palmer, T. D., Gelinas, R. E. & Miller, A. D. (1987) J Virol 61, 1639–1646.
7. Brown, A. M. C. and Scott, M. R. D. (1987) In DNA Cloning, A Practical Approach, Vol. III, pp 189–212.
8. Chang, P. S. et al., (1990), Clin. Biotechnol. 2, 23.
9. Chatterjee, S., Johnson, P. R., and Wong, K. K. Jr. (1992) Science 258, 1485.
10. Chen, C. and Okayama, H. (1987) Mol. Cell. Biol. 7, 2745–2749.
11. Chirgwin, J. J., Przbyla, A. E., MacDonald, R. J. & Rutter, W. J. (1979) Biochemistry 18, 5295.
12. Chrisley, L. A. (1991) Antisense Research and Development, 1:65–113.
13. Coffin, J. (1985) In RNA Tumor Viruses, eds. Weis, R., Teich, N., Varmus, H. and Coffin, J. (Cold Spring Harbor Lab., Cold Spring Harbor, N.Y.), Vol. 2, pp 766–782.

14. Crisell, P. et al. (1993) Nucl. Acids. Res. 21, 5251–5255.
15. Curiel, T. et al. (1992) Hum. Gene Ther. 3, 147.
16. Danos, O. & Mulligan, R. C. (1988) Proc Natl Acad Sci USA 85, 6460–6464.
17. Debouck, C. (1992) Aids Research and Human Retroviruses 8, 153–164.
18. Dropulic, B., Lin, N. H., Martin, M. A. and Jeang, K.-T. (1992) J. Virol. 66, 1432–1441.
19. Egholm, (1992) J. Am. Chem. Soc. 114:1895.
20. Epstein, F. H. (1991) The New England J. Med. 324, 308–317.
21. Freed, E., Delwart, E., Buchschacher, G. Jr., and Panganiban, A., (1992) Proc. Natl. Acad. Sci. U.S.A. 89, 70.
22. Gautsch, J. W. and Meier, H. (1976) Virology 72, 509–513.
23. Gallo, R. C., Salahuddin, S. Z, Popovic, M., Shearer, G. M., Kaplan, M., Haynes, B. F., Palker, T. J., Redfield, R., Oleske, J., Safai, B., White, G., Foster, P. & Markham, P. D. (1984) Science 224, 500–503.
24. Goodchild, J. et al., (1988) Proc. Natl. Acad. Sci. U.S.A. 85, 5507.
25. Gordon et al. (1987) Bio/Technology 5:1183.
26. Greene, W. C. (1990) Annu. Rev. Immunol. 8, 453–475.
27. Hammer et al. (1985) Nature 315:680.
28. Hampel, A. et al. (1990) Nucleic Acid Res. 18, 299–304.
29. Han, L., Yun, J. S. and Wagner, T. E. (1991) Proc. Natl. Acad. Sci. USA 88, 4313–4317.
30. Hanvey et al., (1992) Science 258:1409–1548.
31. Harrison, G. P. and Lever, A. M. L. (1992) J. Virol. 66, 4144–4153.
32. Haseloff, J. and Gerlach, W. J. (1988) Nature (London) 334, 585–591.
33. Johnson, V. A. & Byington, R. E. (1990) In Techniques in HIV Research, eds. Aidovini, A. & Walker, B. D. (Stockton Press, New York) pp 71–76.
34. Jones, K. A. (1989) The New Biologist 1, 127–135.
35. Kotlin, R. M. et al. (1990) Proc. Natl. Acad. Sci. U.S.A. 87, 2211.
36. Levy, J. A. (1984) Science 225, 840.
37. Levy, J. A. (1993) Microbiological Rev. 57, 183–289.
38. Lisziewicz, J., Rappaport, J. & Dhar, R. (1991) New Biol. 3, 82–89.
39. Lisziewicz, J., Sun, D., Smythe, J., Lusso, P., Lori, F., Louie, A., Markham, P., Rossi, J., Reitz, M. & Gallo, R. C. (1993) Proc Natl Acad Sci USA 90, 8000–8004.
40. Lo, K. M. S., Blasolo, M. A., Dehni, G., Palu, G. and Haseltine, W. A. (1992) J Virology 190, 176–183.
41. Malim, M. H. et al., (1992) J. Exp. Med. 176, 1197.
42. Malim, M. H., Bohnlein, S., Hauber, J., and Cullen, B. R. (1989) Cell 58, 205.
43. Mann, R., Mulligan, R. C. & Baltimore, D. (1983) Cell 33, 153–159.
44. Marshall, W. S. and Caruthers, M. H., (1993) Science 259, 1564.
45. McClure, M. O., Moore, J. P., Blanc, D. F., Scotting, P., Cook, G. M. W., Keynes, R. J., Weber, J. N., Davies, D. and Weiss, R. A. (1992) Aids Research and Human Retroviruses 8, 19–26.
46. McCune, J. M. (1991) Cell 64, 351–363.
47. Miller, A. D. & Rosman, G. J. (1989) Biotechniques 7, 980–990.
48. Miller, D. (1992) Nature 357, 455–460.
49. Miller, A. D. (1992) Current Topic in Microbiology and Immunology 158, 1–24.
50. Nielson, (1991) Science 254:1497.
51. Ojwang, J. O., Hampel, A., Looney, D. J., Wong-Staal, F. and Rappaport, J. (1992) Proc. Natl. Acad. Sci. USA 89, 10802–10806.
52. Perriman, R., Delves, A. and Gerlach, W. L. (1992) Gene 113, 157–163.
53. Peterlin, B. M. and Luciw, P. A. (1988) Bio/Technology 6, 794–799.
54. Pittius et al. (1988) PNAS 85:5874.
55. Poznansky, M., Lever, A., Bergeron, L., Haseltine, W., and Sodroski, J. (1991) J. Virol. 65, 532.
56. Pyle, A. M. (1993) Science 261, 709–714.
57. Reed, K. C. and Mann, D. A. (1985) Nucleic Acids Res. 13, 7207–7221.
58. Rhodes, A. & James, W. (1991) AIDS 5, 145–151.
59. Rossi, J. J., Elkins, D., Zaia, J. A. and Sullivan, S. (1992) In Aids Research and Human Retroviruses 8, 183–189.
60. Rossi, J. J. and Sarver, N., (1992) Innovations in Antiviral Development and the Detection of Virus Infection, 95–109.
61. Saenger, W. (1984) Principles of Nucleic Acid Structure (Springer, New York).
62. Sarver, N., Cantin, E. M., Chang, P. S., Zaia, J. A., Ladne, P. A., Stephens, D. A. and Rossi, J. J. (1990) Science 247, 1222–1225.
63. Sczakiel, G., Oppenländer, M., Rittner, K. and Pawlita, M. (1992) J. Virol. 66, 5576–5581.
64. Simons et al. (1987) Nature 328:530.
65. Simons et al. (1988) Bio/Technology 6:179.
66. Sioud, M. and Drlica, K. (1991) Proc. Natl. Acad. Sci. USA 88, 7303–7309.
67. Steffy, K. R. and Wong-Staal, F., (1993) J. Virol. 67, 1854.
68. Stevenson, M., Bukrinsky, M. and Haggerty, S. (1992) Aids Research and Human Retroviruses 8, 107–117.
69. Sullenger, B. A., Gallardo, H. F., Ungers, G. E. and Gilboa, E. (1991) J. Virol. 65, 6811.
70. Sullenger, B. A., Gallardo, H. F., Ungers, G. E. and Gilboa, E. (1990) Cell 63, 601–608.
71. Sullenger, B. A. et al. (1993) Science 262, 1567–1569.
72. Teich, N., Wyke, J., Mak, T., Bernstein, A. and Hardy, W. (1985) In RNA Tumor Viruses, eds. Weiss, R., Teich, N., Varmus, H. and Coffin, J. (Cold Spring Harbor Lab., Cold Spring Harbor, N.Y.) Vol. 1, pp 901–923.
73. Trono, D., Feinberg, M., and Baltimore, D., (1989) Cell 59, 113.
74. Uhlmann, E. and Peyman, A., (1990) Antisense Oligonucleotides: A New Therapeutic Principle. Chemical Reviews 90:543–584.
75. Van Brunt, J. Molecular Farming: Transgenic Animals as Bioreactors. Bio/Technology 6:1149–1154.

76. Van der Krol, J., Mol, N., Stuitje, A. R., (1988) BioTechniques 6, 958.
77. Warrilow, D., Takayama, Y. and Symonds, G. (1992) BioTechniques 13, 42–43.
78. Weerasinghe, M., Liem, S. E., Asad, S., Read, S. E. and Joshi, S. (1991) J. Virol. 65, 5531–5534.
79. Yamada, O., Yu, M., Yee, J. Kraus, G., Looney, D. & Wong-Staal, F. (1994) Gene Therapy 1, 38–45.
80. Yee, J. K. et al. (1987) Proc Natl Acad Sci Usa 84, 5179–5201.
81. Yu, M., Ojwang, J. O., Yamada, O., Hampel, A., Rappaport, J., Looney, D. & Wong-Staal, F. (1993) Proc. Natl. Acad. Sci. USA 90, 6340–6344.
82. Yu, M., Poeschla, E. & Wong-Staal, R. (1994) Gene Therapy 1, 13–26.
83. Zhou, C. et al. (1992) Proc. Third International Symposium on Catalytic RNA (Ribozymes) and Targeted Gene Therapy for Treatment of HIV Infection.
84. Zuker, M. and Stiegler, P. (1981) Nucleic Acid. Res. 9, 133–148.

What is claimed:

1. A cell comprising a viral vector producing a non-naturally occurring RNA compound which comprises nucleotides whose sequence defines a catalytic region and nucleotides whose sequence comprises sequences complementary to both a first nucleotide sequence directly 3' and a second nucleotide sequence 5' of a target site in a target molecule of a MoMLV or a HIV RNA virus, wherein the target site comprises three nucleotides of which the 5' nucleotide is selected form the group consisting of nucleotide numbers 274 and 366 of the MoMLV packaging sequence, and nucleotide number 5849 of the HIV tat gene, wherein the non-naturally occurring RNA compound inactivates the target molecule in the cell.

2. The cell of claim 1, wherein the compound has the structure (SEQ ID NO:1):

$$3'\text{-}(X)_n\text{A} \quad (X)_{n'}\text{-}5'$$
$$\begin{array}{c} | \\ A \\ | \\ A \\ | \\ G \\ | \\ X \quad * \quad X \\ | \quad \quad | \\ (X)_m \quad * \quad (X)_{m'} \\ \quad \backslash \quad / \\ \quad (X)_b \end{array} \begin{array}{c} C \\ \backslash \\ U \\ \quad \backslash \\ \quad (X)_a \quad G \\ \quad / \quad \backslash \\ A \quad \quad A \\ \quad \backslash \quad / \\ \quad G\text{—}X \end{array}$$

wherein each X represents a ribonucleotide which is the same or different;

wherein each of A, C, U, and G represents a ribonucleotide;

wherein 3'—AAG . . . AGUCX—5' defines the catalytic region;

wherein $(X)_n$A defines nucleotides whose sequence comprises a sequence which hybridizes to a nucleotide sequence directly 5' of the 3' nucleotide of the target site within the MoMLV packaging sequence or the HIV tat gene, and n defines the number of nucleotides;

wherein $(X)_{n'}$ defines nucleotides whose sequence comprises a sequence which hybridizes to a nucleotide sequence directly 3' of the target site within the MoMLV packaging sequence or the HIV tat gene, and n' defines the number of nucleotides;

wherein each * represents base pairing between the nucleotides located on either side thereof;

wherein each solid line represents a covalent bond between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents an integer which is greater than or equal to 1; and wherein $(X)_b$ represents an oligonucleotide and b represents an integer which is greater than or equal to 2.

3. The cell of claim 1, wherein the compound has the structure (SEQ ID NO:2):

$$3'\,(X)_n\text{—A} \quad (X)_{n'}\,5'$$
$$\begin{array}{c} | \\ A \\ | \\ A \\ | \\ G \end{array} \begin{array}{c} \\ C \\ \backslash \\ U \\ \quad \backslash \\ \quad G \\ / \quad \backslash \\ A \quad \quad A \\ \backslash \quad / \\ G\text{—}X \end{array}$$
$$\quad \backslash (X)_m /$$

wherein each X is the same or different and represents a ribonucleotide;

wherein each of A, C, U, and G represents a ribonucleotide;

wherein 3'—AAG . . . AGUCX—5' defines the catalytic region;

wherein $(X)_n$A defines nucleotides whose sequence comprises a sequence which hybridizes to a nucleotide sequence directly 5' of the 3' nucleotide of the target site within the MoMLV packaging sequence or the HIV tat gene, and n defines the number of nucleotides;

wherein $(X)_{n'}$ defines nucleotides whose sequence comprises a sequence which hybridizes to a nucleotide sequence directly 3' of the target site within the MoMLV packaging sequence or the HIV tat gene, and n defines the number of nucleotides;

wherein each solid line represents a covalent bond between the nucleotides located on either side thereof; and wherein m represents an integer from 2 to 20; and wherein none of the nucleotides $(X)_m$ are Watson-Crick base paired to any other nucleotide within the compound.

4. The cell of claim 1, wherein the compound has the structure (SEQ ID NO:3):

$$\begin{array}{c} (X)_{P3}\text{-AXAXUAC-}(X)_{P4}3' \\ (X)_{L2} \quad * \quad \quad \quad * \\ \quad (X)_{P2}\text{-CAAAC-}(X)_{P1}\text{—}(X)_{F4}\text{—AG—}(X)_{F3}\text{-}5' \end{array}$$

wherein each X is the same or different and represents a ribonucleotide;

wherein each of A, C, U, and G represents a ribonucleotide;

wherein 3'$(X)_{P4}$ . . . $(X)_{P1}$—5' defines the catalytic region;

wherein $(X)_{F4}$ defines the nucleotides whose sequence comprises a sequence complementary to a nucleotide sequence 5' of the target site in the target molecule of the MoMLV or HIV RNA virus;

wherein $(X)_{F3}$ defines the nucleotides whose sequence comprises a sequence complementary to a nucleotide sequence directly 3' of the target site in the target molecule of the MoMLV or HIV RNA virus;

wherein F3 represents an integer which defines the number of nucleotides in the oligonucleotide with the proviso that F3 is greater than or equal to 3;

wherein F4 represents an integer which defines the number of nucleotides in the oligonucleotide with the proviso that F4 is from 3 to 5;

wherein each of $(X)_{P1}$ and $(X)_{P4}$ represents an oligonucleotide having a predetermined sequence such that $(X)_{P4}$ base-pairs with 3–6 bases of $(X)_{P1}$;

wherein P1 represents an integer which defines the number of nucleotides in the oligonucleotide with the proviso that P1 is from 3 to 6 and the sum of P1 and F4 equals 9;

wherein each of $(X)_{P2}$ and $(X)_{P3}$ represents an oligonucleotide having a predetermined sequence such that $(X)_{P2}$ base-pairs with at least 3 bases of $(X)_{P3}$;

wherein each * represents base pairing between the nucleotides located on either side thereof;

wherein each solid line represents a chemical linkage providing covalent bonds between the nucleotides located on either side thereof;

wherein each of the dashed lines independently represents either a chemical linkage providing covalent bonds between the nucleotides located on either side thereof or the absence of any such chemical linkage; and wherein $(X)_{L2}$ represents an oligonucleotide which may be present or absent with the proviso that L2 represents an integer which is greater than or equal to 3 if $(X)_{L2}$ is present.

5. The cell of claim 1, wherein the nucleotides whose sequence defines a catalytic region are from a hepatitis delta virus conserved region.

6. The cell of claim 1, wherein the catalytic region contains the sequence NCCA at its 3' terminus.

7. The cell of claim 1, wherein the compound is covalently linked to an antisense nucleic acid compound that hybridizes to a predetermined sequence of the MoMLV or HIV virus located 3' or 5' of the target site.

8. The cell of claim 1, wherein the cell is a human cell and the virus is HIV, and wherein the compound further comprises at least one additional catalytic region, with or without an antisense molecule covalently linked thereto, and targeted to a different region of the genome of the HIV virus.

9. The cell of claim 8, wherein the different region of the HIV genome is selected from the group consisting of long terminal repeat, 5' untranslated region, splice donor-acceptor sites, primer binding sites, 3' untranslated region, gag, pol, protease, integrase, env, tat, rev, nef, vif, vpr, vpu, vpx, and tev region.

10. The cell of claim 9, wherein each of the additional catalytic regions is linked to nucleotide sequences complementary to both a first nucleotide sequence directly 3' and a second nucleotide sequence 5' of a target site wherein the 5' nucleotide of the target site is selected from the group consisting of nucleotide numbers 5792, 5849, 5886, and 6042 in the HIV tat region and nucleotide number 749 in the HIV packaging sequence.

11. A cell comprising a viral vector which produces a non-naturally occurring RNA compound which comprises two or more domains which may be the same or different wherein at least one domain comprises nucleotides whose sequence defines a catalytic region and nucleotides whose sequence comprises sequences complementary to both a first nucleotide sequence directly 3' and a second nucleotide sequence 5' of a target site in a target molecule of a MoMLV or a HIV RNA virus, wherein the target site consists of three nucleotides of which the 5' nucleotide is selected form the group consisting of nucleotide numbers 274 and 366 of the MoMLV packaging sequence, and nucleotide number 5849 of the HIV tat gene, wherein the non-naturally occurring RNA compound inactivates the target molecule in the cell.

12. A human cell resistant to HIV infection comprising a viral vector producing a non-naturally occurring RNA compound which comprises nucleotides whose sequence defines a catalytic region that catalyzes RNA cleavage and nucleotides whose sequence defines a first nucleotide sequence that hybridizes to a first portion of SEQ ID NO. 10 and a second nucleotide sequence that hybridizes to a second portion of SEQ ID NO. 10, wherein the non-naturally occurring RNA compound inactivates an HIV tat gene comprising SEQ ID NO. 10 in the human cell, thus making the human cell resistant to HIV infection.

* * * * *